US008821586B2

(12) United States Patent
Bjursten et al.

(10) Patent No.: US 8,821,586 B2
(45) Date of Patent: Sep. 2, 2014

(54) POROUS IMPLANT GRAIN OR GRANULE

(75) Inventors: Lars Magnus Bjursten, Limhamm (SE); Bengt Mjöberg, Ystad (SE); Niklas Axén, Järlåsa (SE)

(73) Assignee: Tigran Technologies AB, Malmo (SE)

( * ) Notice: Subject to any disclaimer, the term of this patent is extended or adjusted under 35 U.S.C. 154(b) by 1251 days.

(21) Appl. No.: 12/071,507

(22) Filed: Feb. 21, 2008

(65) Prior Publication Data
US 2008/0294271 A1 Nov. 27, 2008

Related U.S. Application Data

(63) Continuation-in-part of application No. PCT/SE2007/000984, filed on Nov. 6, 2007.

(60) Provisional application No. 60/902,500, filed on Feb. 22, 2007.

(30) Foreign Application Priority Data

Feb. 22, 2007 (SE) ........................................ 0700457

(51) Int. Cl.
*A61F 2/02* (2006.01)

(52) U.S. Cl.
USPC .................... 623/23.74; 623/23.75; 623/11.11

(58) Field of Classification Search
CPC ............ A61F 10/00023; A61K 9/0024; A61L 2300/406; A61L 2300/41; A61L 2300/412; A61L 27/06; A61L 27/54; A61L 27/56
USPC ................................. 623/23.74, 23.75, 11.11
See application file for complete search history.

(56) References Cited

U.S. PATENT DOCUMENTS

| | | | |
|---|---|---|---|
| 5,015,256 A | 5/1991 | Bruce et al. | |
| 5,118,667 A | 6/1992 | Adams | |
| 7,192,445 B2 * | 3/2007 | Ellingsen et al. | 623/11.11 |
| 2003/0082122 A1 * | 5/2003 | Chopin et al. | 424/63 |
| 2005/0031663 A1 * | 2/2005 | Larsson et al. | 424/423 |
| 2005/0228111 A1 | 10/2005 | Furuzono et al. | |
| 2005/0234558 A1 * | 10/2005 | Petersson et al. | 623/23.5 |
| 2006/0161256 A1 | 7/2006 | Ziegler et al. | |
| 2006/0286051 A1 | 12/2006 | Tanaka et al. | |
| 2007/0003752 A1 | 1/2007 | Bruce et al. | |

FOREIGN PATENT DOCUMENTS

| | | |
|---|---|---|
| EP | 0 501 595 A1 | 9/1992 |
| EP | 0501595 A1 | 9/1992 |
| EP | 0856 299 | 8/1998 |
| EP | 2068895 | 3/2008 |
| WO | 89/06548 | 7/1989 |
| WO | 89/06548 A1 | 7/1989 |
| WO | 98/51231 | 11/1998 |
| WO | 99/34845 | 7/1999 |
| WO | 00/64504 | 11/2000 |
| WO | 03/063925 A1 | 8/2003 |
| WO | WO 03/078327 A1 | 9/2003 |
| WO | 2006/026840 A2 | 3/2006 |
| WO | 2006126312 | 11/2006 |
| WO | WO 2006/121330 A2 | 11/2006 |
| WO | WO 2008/056987 A2 | 5/2008 |

OTHER PUBLICATIONS

Oh et al "Significantly accelerated osteoblast cell growth on aligned TiO2 nanotubes," Journal of Biomedical Materials Research Part A DOI 10.1002/jbm.A, published online Apr. 6, 2006.*
Invoice defining delivery of titanium sponge powder from Hereford Metal Powder Company Limited to Bruce Medical AB, May 17, 2001. Hereford Metal Powder Company Limited.
Photographs submitted as evidence in the Opposition Submission in EP1980276 (2011).
Results from Surface Area Measurements Conducted on Titanium Sponge Powder from Hereford Metal Powder Company Limited. Feb. 25, 2010.
Sahlin, H. et al. (2006) "Anti-inflammatory Properties of Micropatterned Titanium Coatings" Journal of BiomedicalMaterials Research, 77:43-49.
Tigran Technologies AB (2006) "Inbjudan till förvärv av ktier i Tigran Technologies AB".
Results from Surface Area Measurements Conducted on Porous Titanium Granules Marketed by Tigran Technologies as Natix. Jan. 3, 2010.
Tengvall, P. et al. (1990) "Bactericidal Properties of a Titanium-Peroxy Gel Obtained from Metallic Titanium and Hydrogen Peroxide" Journal of Biomedical Materials Research, 24:319-330.
Tengvall, P. et al. (1991) "A Model for the Interaction Between Titanium and Living Systems" Biofouling, 4:219-223.
Overgaard, L. et al. (1998) "Anti-Inflammatory Properties of Titanium in the Joint Environment" The Journal of Bone and Joint Surgery (Br) 888-893.
Larsson, J. et al. (2004) "Anti-Inflammatory Effects of a Titanium-peroxy Gel: Role of Oxygen Metabolites and Apoptosis" Journal of Biomedical Materials Research, 68:448-457.
Juodzbalys, G. et al. (2003) "New Acid Etched Titanium Dental Implant Surface" Stomatologija, Baltic Dental and Maxiloofacial Journal, 5(3):101-105.

(Continued)

*Primary Examiner* — Suzanne Ziska
(74) *Attorney, Agent, or Firm* — Smith, Gambrell & Russell, LLP.

(57) ABSTRACT

An implant with anti-inflammatory or antibacterial effects, or both, for implantation in a human or animal body, the implant having a set of porous grains or granules, wherein at least a plurality of the porous grains or granules include titanium, one or more titanium oxides or titanium alloy and have a titanium oxide layer on their surface and have a mean length from one side to the opposite side, through a geometrical center, of at least 200 μm and up to 5 mm and a mean specific surface area of at least 0.15 m2/g according to the BET method. Also featured is a population of grains or granules having anti-inflammatory or antibacterial effects, or both. Further featured is a method of producing an implant, a method for deriving a population of grains or granules, and a method for treating a condition with a porous grain or granule.

35 Claims, 10 Drawing Sheets

(56) References Cited

OTHER PUBLICATIONS

Gonzalez, J. et al. (2006) "Removal Torque and Physico-Chemical Characteristics of Dental Implants Etched with Hydrofluoric and Nitric Acid. An Experimental Study in Beagle Dogs" Medicina Oral, Patalogia Oral y Cirugia Bucal, 11: E281-285.
Fracassi, F. et al. (1992), "Chemistry of Titanium Etching in Fluorinated and Chlorinated Gases" Pure and Applied Chemistry 64:703-707.
Chiesa, R. et al. (2003) "Osteointegration of Titanium and its Alloys by Anodic Spark Deposition and Other Electrochemical Techniques: A Review" Journal of Applied Biomaterials and Biomechanics, 1:91-107.
Cai, Q. et al. (2005) "The Effect of Electrolyte Composition on the Fabrication of Self-Organized Titanium Oxide Nanotube Arrays by Anodic Oxidation" Journal of Materials Research. 20:230-236.
Tengvall, P. et al. (1989) "Titanium Gel Made from Metallic Titanium and Hydrogen Peroxide" Journal of Colloid and Interface Science, 130:405-413.
Tengvall, P. et al. (1989) "Interaction Between Hydrogen Peroxide and Titanium: a Possible Role in the Biocompatibility of Titanium" Biomaterials, 10:118-120.
W.B. Saunders Company (2000) "Dorland's Illustrated Medical Dictionary" 29th Ed. pp. 186, 900-901, 1700, 1909.
Wikipedia (2011) "Ultraviolet" http://en.wikipedia.org/wiki/ultraviolet, cited Dec. 20, 2011.
Citizdendium (2009) "Testosterone" http://en.citizendium.org/wiki/Testosterone, cited Nov. 14, 2009.
Drugs-About.com (2009) "Andronate" http://drugs-about.com/drugs-a/andronate.html, cited Nov. 14, 2009.
Arweiler, N. et al. (2002) "Antibacterial Effect of an Enamel Matrix Protein Derivative on in vivo Dental Biofilm Vitality" Clinical Oral Investigations, 6:205-209.
Spahr, A. et al. (2002) Effect of the Enamel Matrix Derivative Emdogain on the Growth of Periodontal Pathogens in vitro Journal of Clinical Periodontology, 29:62-72.
Merriam-Webster (2002) "Merriam-Webster's Collegiate Dictionary" Merriam-Webster, 10th Ed. p. 600.
Rowe, R. et al. (2006) "Handbook of Pharmaceutical Excipients" 5th Ed. 671-674.
Reddi, A. et al. (1997) "Bone Morphogenetic Proteins: an Unconventional Approach to Isolation of First Mammalian Morphogens" Cytokine & Growth Factor Reviews, 8:11-20.
Bessa, et al. (2008) "Bone Morphogenetic Proteins in Tissue Engineering: the Road from the Laboratory to the Clinic, Part I (basic concepts)" Journal of Tissue Engineering and Regenerative Medicine, 2:1-13.
Wikipedia (2011) "Titanium Dioxide" http://en.wikipedia.org/wiki/Titanium_dioxide, cited Dec. 13, 2011.
Rocker, et al. (1987) "Titanium Overlayers on TiO2(110)" Surface Science, 181:530-558.
Mayer, et al. (1995) "Titanium and Reduced Titania Overlayers on Titanium Dioxide(110)" Journal of Electron Spectroscopy and Related Phenomena, 73:1-11.
Communication of Notice of Opposition in EP1980276 (foreign equivalent to U.S. Appl. No. 12/071,507) mailed Dec. 30, 2011.
Notice of Opposition in EP1980276 (foreign equivalent to U.S. Appl. No. 12/071,507) mailed Dec. 21, 2011.
Notice of Reasons for Rejection for Japanese Patent Application No. 2009-550829 dated Nov. 30, 2012 (in English).
Ruxiong Cal, et al., "Induction of Cytotoxicity by Photoexcited $TiO_2$ Particles[1]", Cancer Research 52, 1992, pp. 2346-2348.
Y. Kubota, et al., "Photokilling of T-24 human bladder cancer cells with titanium dioxide", Br. J. Cancer, 1994, 70, pp. 1107-1111.
Jeti (Japan Energy & Technology Intelligence), ISSN 0289-4343, 1998, vol. 46, No. 10, pp. 66-67.
"Biomedical Application of Dental Treatment Using Free Radical Technology", Kanagawa Odontological Society, 2005, vol. 40, No. 2 pp. 135-138.
M.C. Lee, et al., "Characterization by Electron Spin Resonance Spectroscopy of Reactive Oxygen Species Generated by Titanium Dioxide and Hydrogen Peroxide", J. Dent. Res 84(2), 2005, pp. 178-182.
R. Beranek, et al., "Self-Organized Porous Titanium Oxide Prepared in $H_2SO_4$/HF Electrolytes", Electrochemical and Solid-State Letters, 6(3), 2003, pp. B12-B14.
Seisbiro Ito, "Plasma Electrolytic Oxidation of Titanium and Its Application to Photocatalytic Materials", Surface Technology, vol. 56, No. 11, 2005, pp. 631-635.
Dawei Gong, et al., "Titanium oxide nanatube arrays prepared by anodic oxidation", Rapid Communications, J. Mater. Res, vol. 16, No. 12, 2001, pp. 3331-3334.
Vladimir S. Moxson, et al., "Innovations in Titanium Powder Processing", JOM, 2000, pp. 24-26.
Boccaccini, A.R. et al., "Fabrication, characterization and assessment of bioactivity of poly(D,L lactid acid) (PDLLA/$TiO_2$ nanocomposite films" *Composites: Part A: Applied Science and Manufacturing*, vol. 36, No. 6, Jun. 1, 2005, pp. 721-727.
Cai et al., "The effect of electrolyte composition on the fabrication of self-organized titanium oxide nanotube arrays by anodic.oxidation", *J. Mater. Res.*, vol. 20, No. 1, Jan. 2005 (pp. 230-236).
Macak et al., "Smooth Anodic TiO2 Nanotubes", Agnew. Chem. Int. Ed., vol. 44, 2005, pp. 7463-7465.
Chisea et al., "Osteointegration of titanium and its alloys by anodic spark deposition and other electrochemical techniques: A review", Journal of Applied Biomaterials & Biomechanics, vol. 1, 2003, pp. 91-107.
Sittig et al., "Surface characterization of implant materials c.p. Ti, Ti-6AI-7Nb and Ti-6AI-4V with different pretreatments", Journal of Materials Science: Materials in Medicine, vol. 10, 1999, pp. 35-46.
Tengvall, P. et al., "Titanium-hydrogen peroxide interaction: model studies of the influence of the inflammatory response on titanium implants", *Biomaterials*, vol. 10, Apr. 1989, pp. 166-175.
Tengvall, P. et al., "Interaction between hydrogen peroxide and titanium: a possible role in the biocompatibility of titanium", *Biomaterials*, vol. 10, Apr. 1989, pp. 118-120.
Ragai, "Trapped radicals in titania gels", *Nature*, vol. 325, Feb. 1987, pp. 703-705.
Wick, P. et al., "Kinetics Evidence for a Complex between Peroxynitrous Acid and Titanium (IV)", *Inorganic Chemistry*, vol. 43, 2004, pp. 4805-4807.
Tengvall, P. et al., "Physico-chemical Considerations of Titanium as a Biomaterial" *Clinical Materials*, vol. 9, 1992, pp. 115-134.
Simdgren, J-E. et al., "Auger Electron Spectroscopic Studies of the Interface between Human Tissue and Implants of Titanium and Stainless Steel", *Journal of Colloid and Interface Science*, vol. 110, No. 1, 1986, pp. 9-20.
European Search Report corresponding to International Application No. EP 08 15 1660 dated Sep. 8, 2008.
International Search Report corresponding to International Application No. PCT/SE/2007/00984 dated Jun. 13, 2008.

* cited by examiner

Fig A1
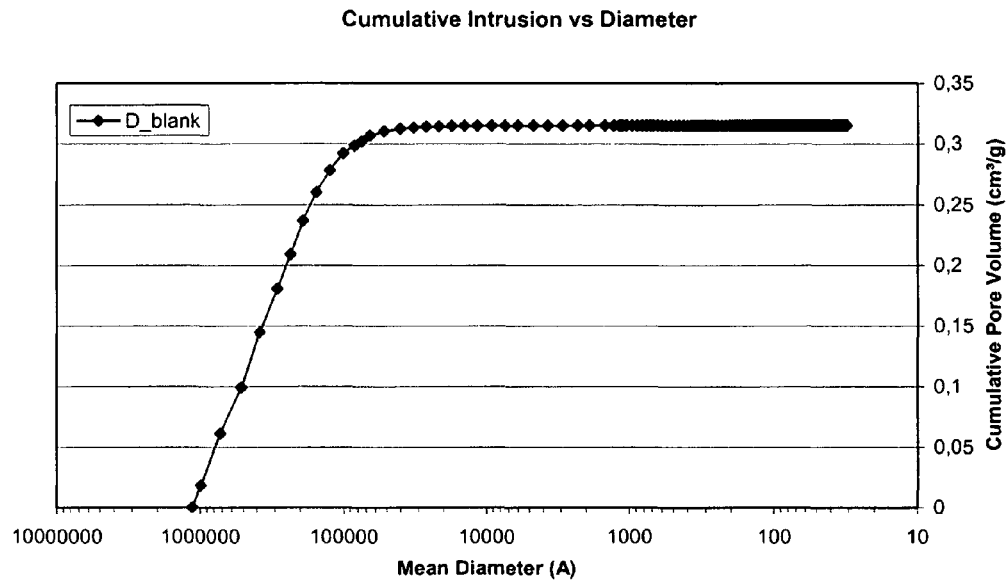
A1 – Cumulative distribution (blank correction)
Fig A2
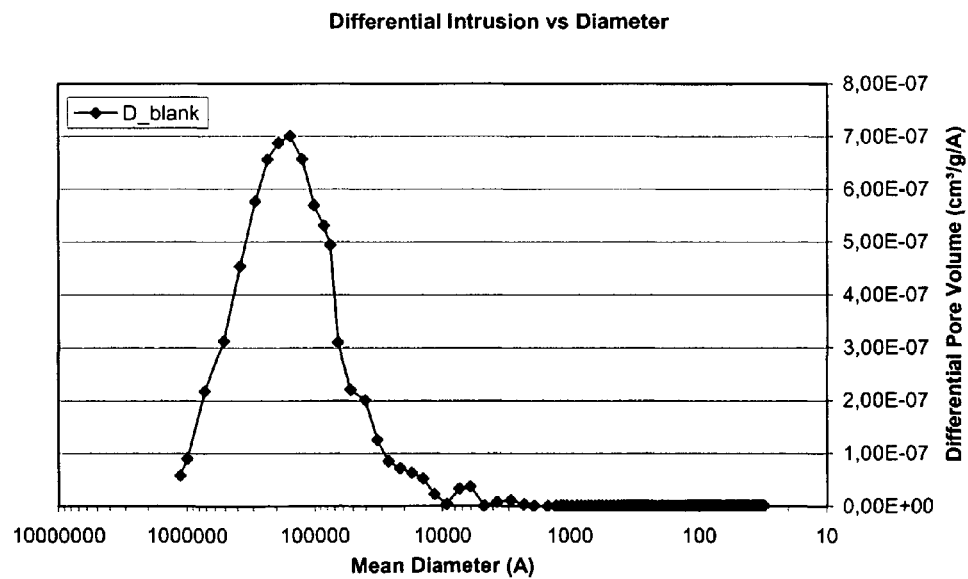
A2 – Differential distribution (blank correction)

Fig B1
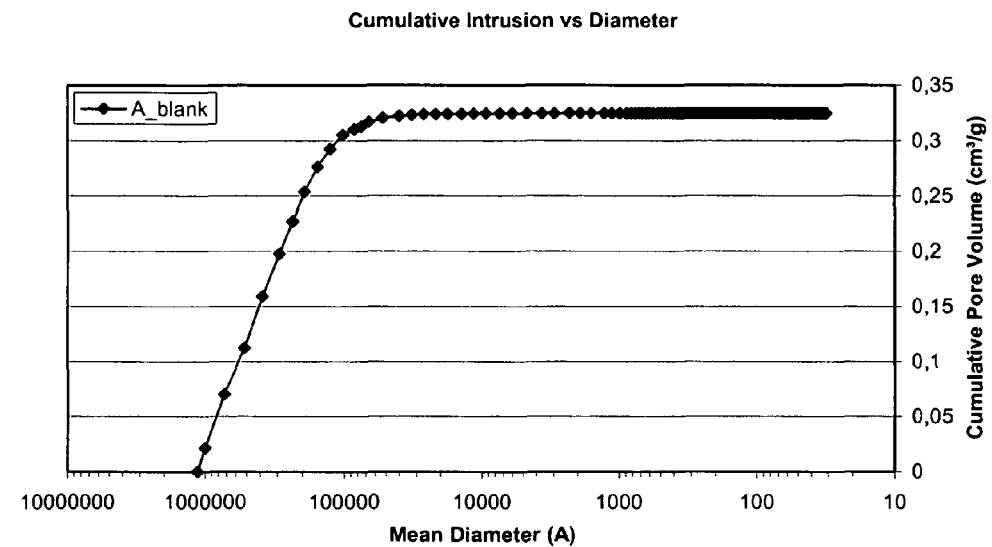
B1 - Cumulative distribution (blank correction)
Fig B2
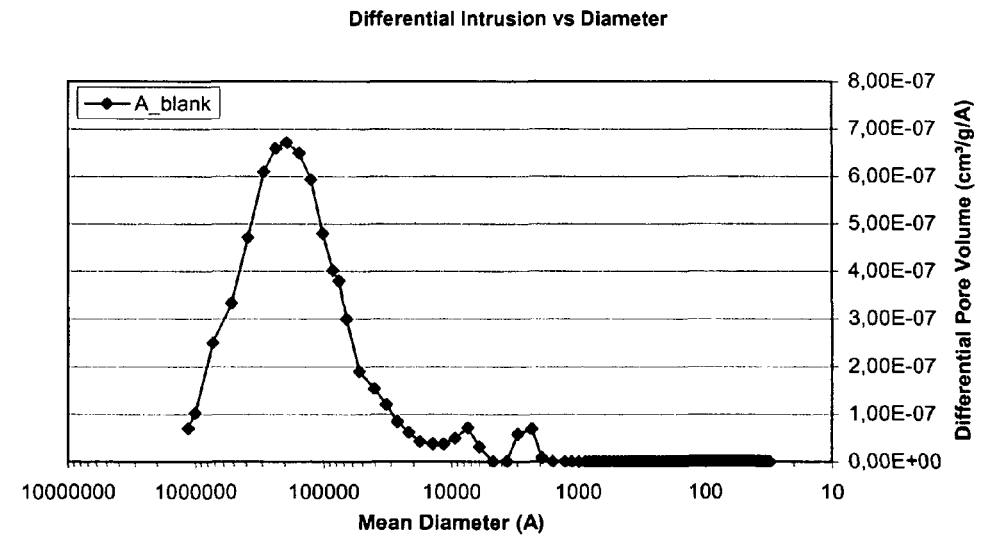
B2 - Differential distribution (blank correction)

Fig C1
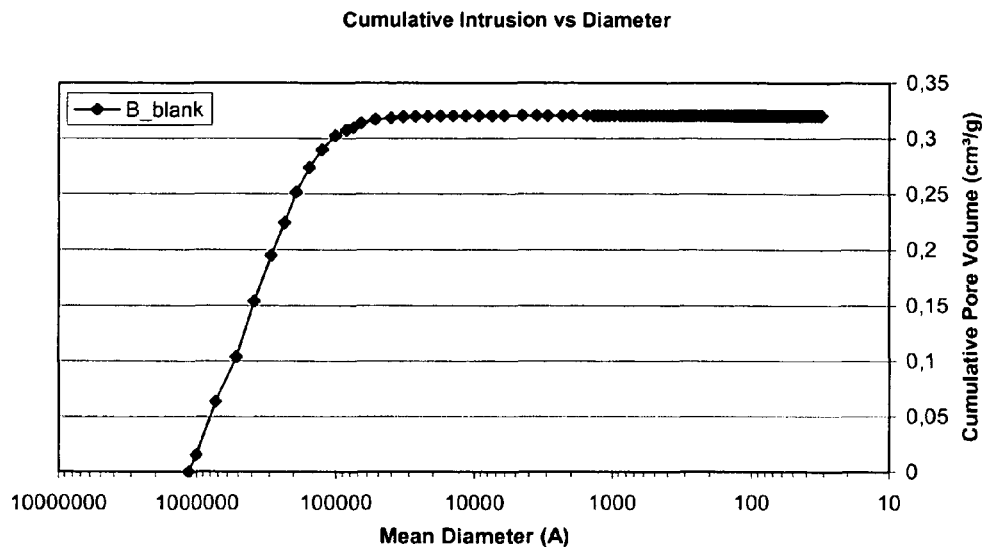
C1 - Cumulative distribution (blank correction)
Fig C2
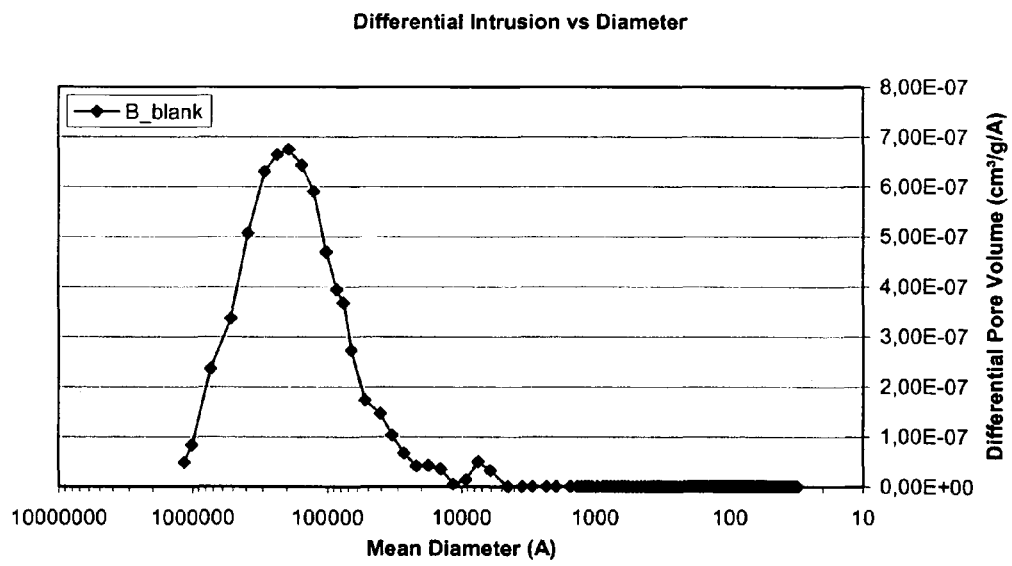
C2 - Differential distribution (blank correction)

Fig D1
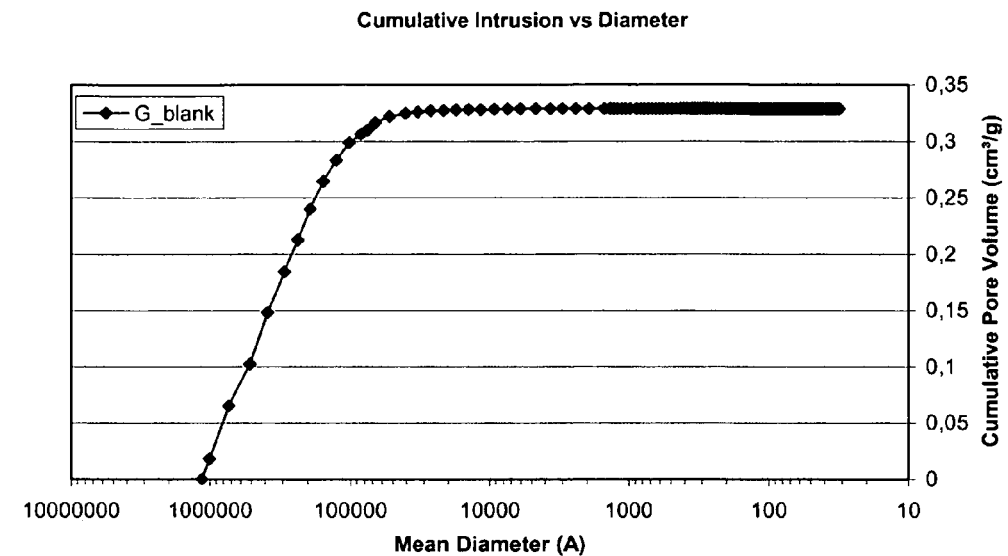
D1 – Cumulative distribution (blank correction)
Fig D2
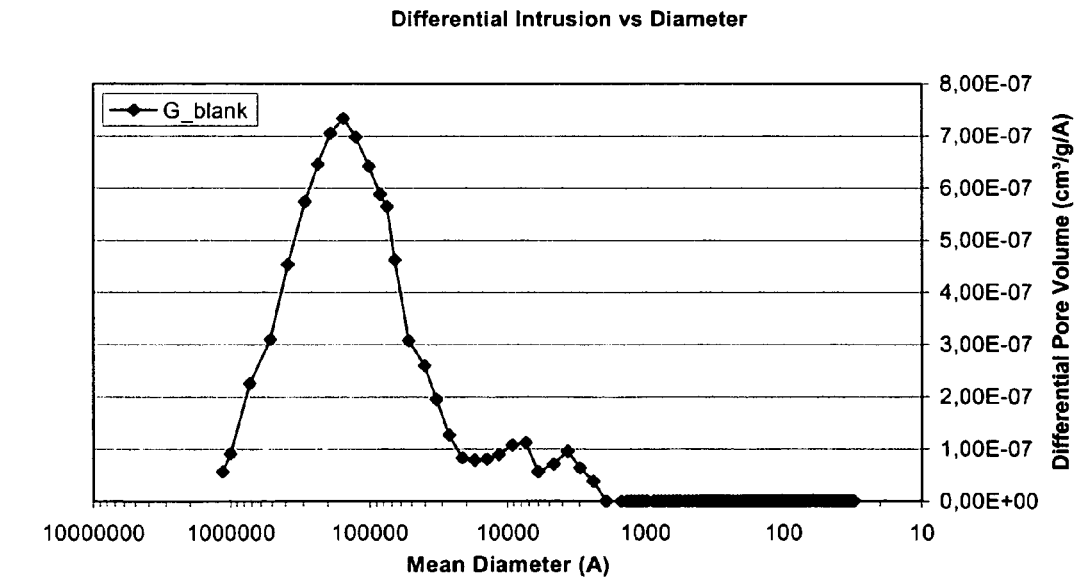
D2 – Differential distribution (blank correction)

Fig E1
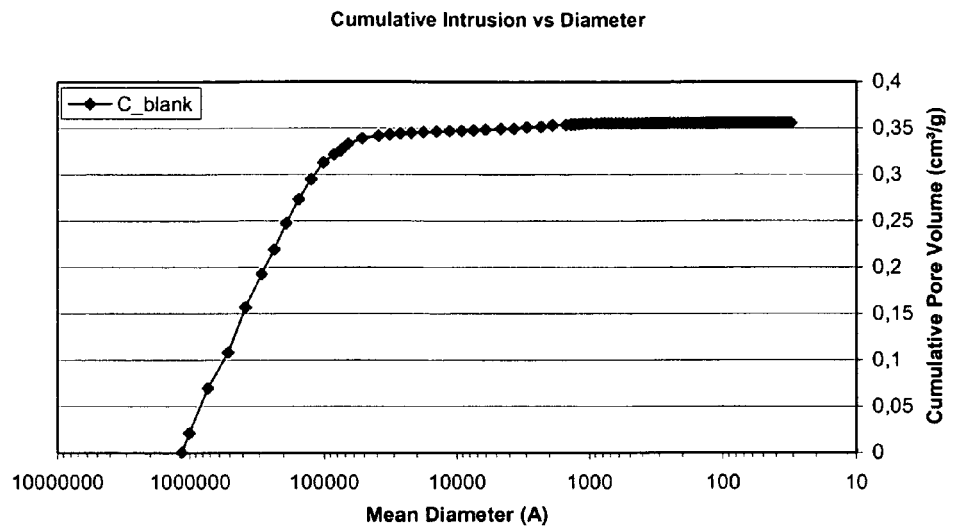
E1 - Cumulative distribution (blank correction)
Fig E2
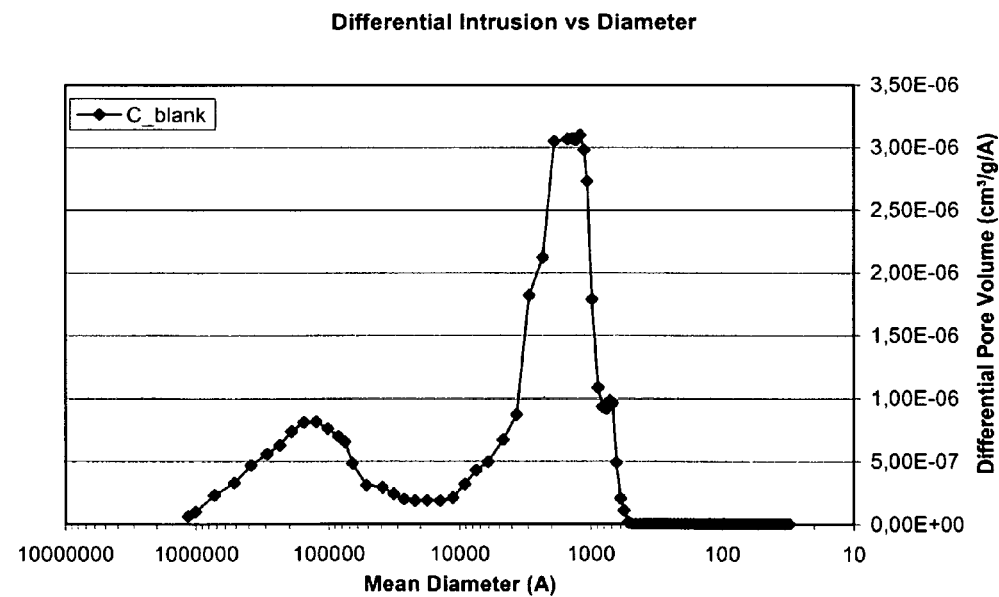
E2 - Differential distribution (blank correction)

Fig F1
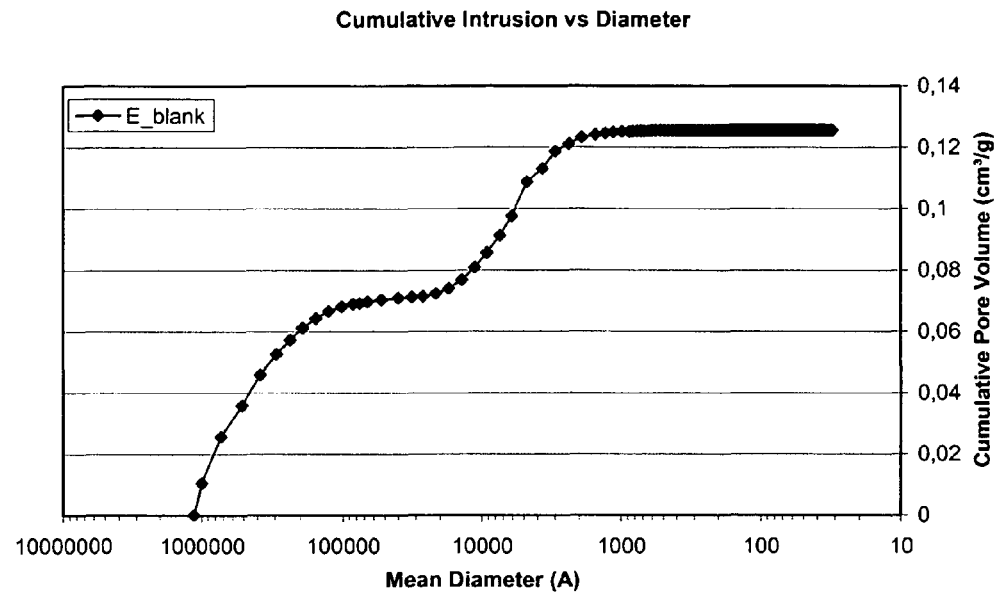
F1 – Cumulative distribution (blank correction)
Fig F2
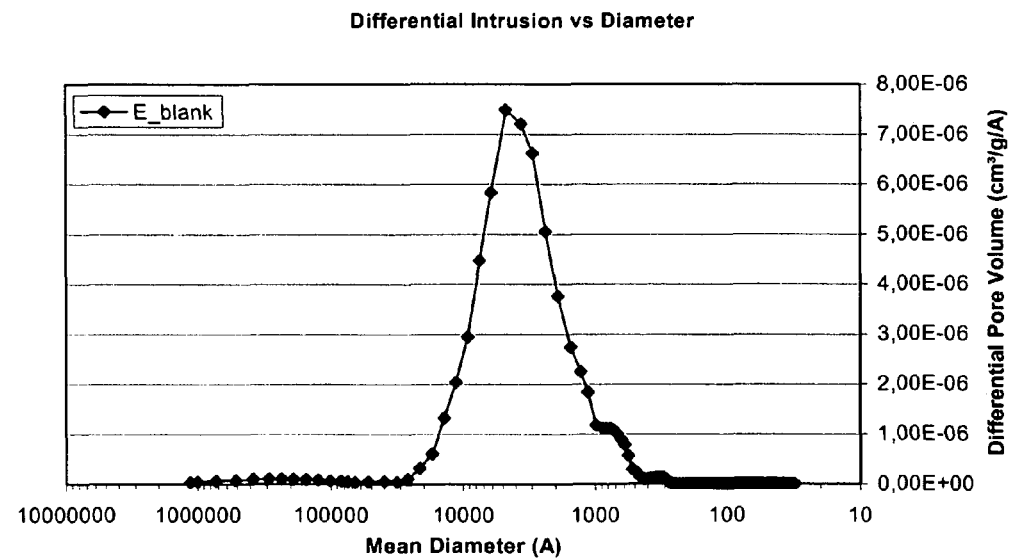
F2 – Differential distribution (blank correction)

Fig F3
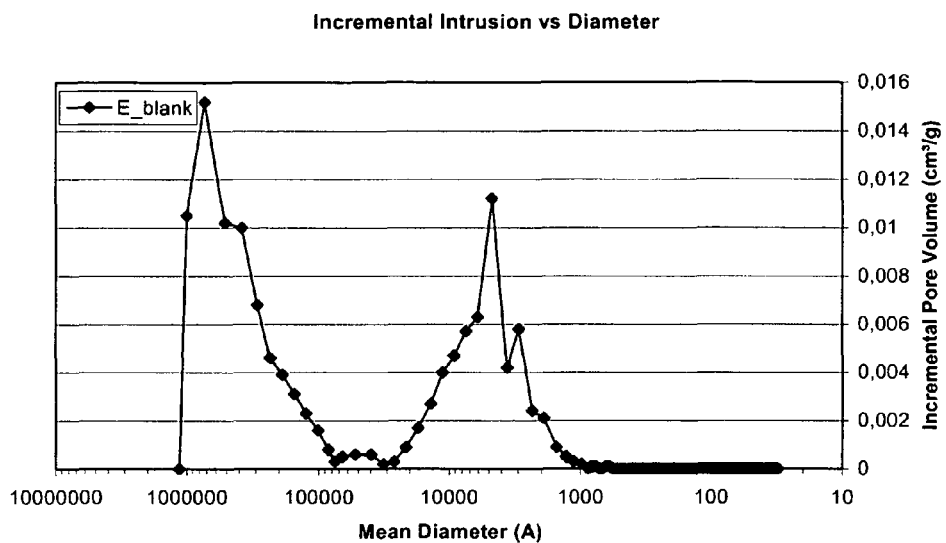
F3 - Incremental distribution (blank correction)

Fig G1 – Commercially available grain, start material 2
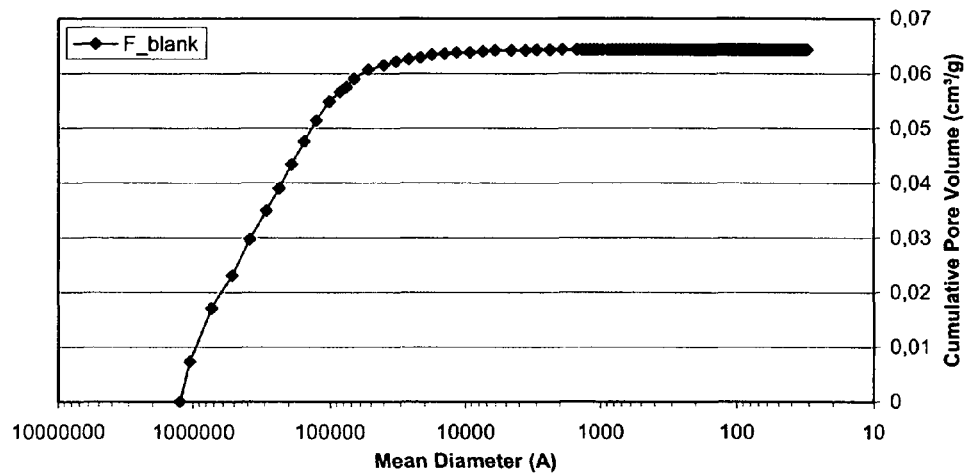
G1 – Cumulative distribution (blank correction)
Fig G2 – Commercially available grain, start material 2
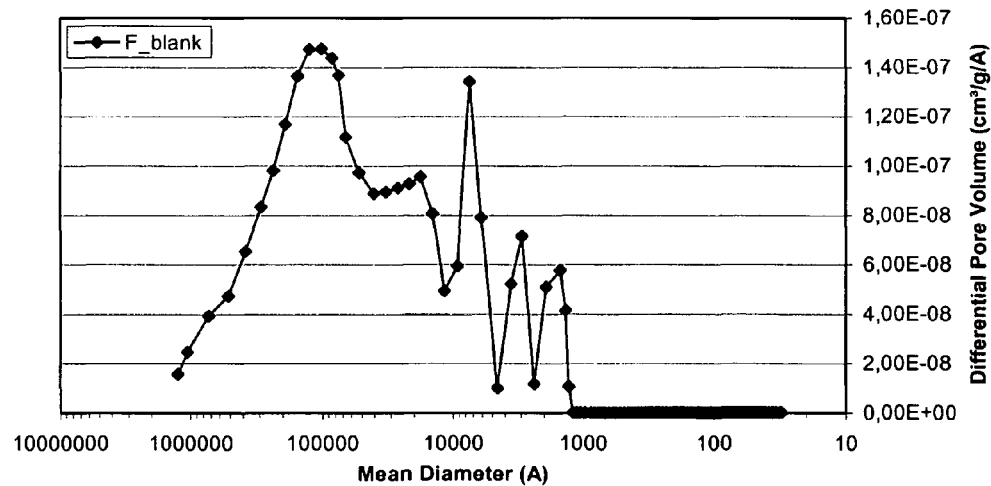
G2 – Differential distribution (blank correction)

Fig H1
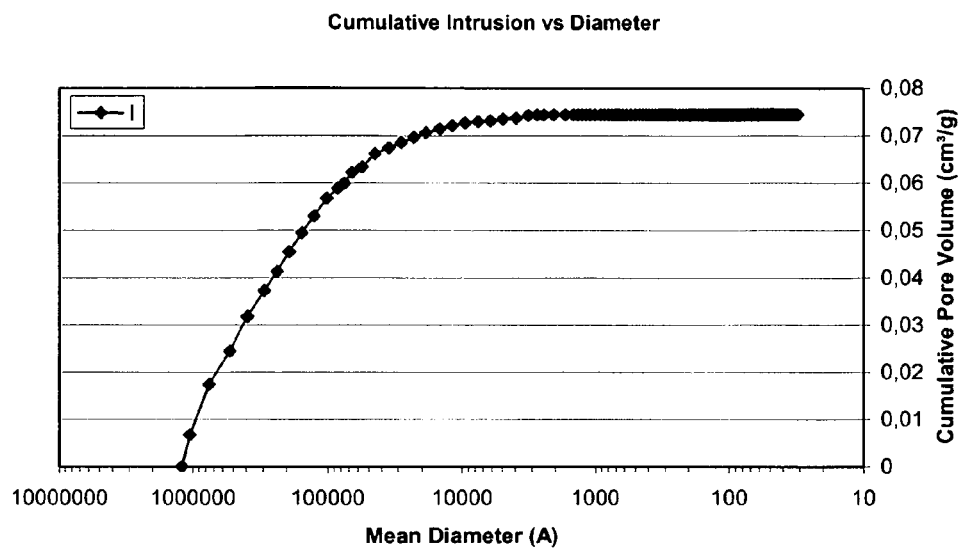
H1 – Cumulative distribution
Fig H2
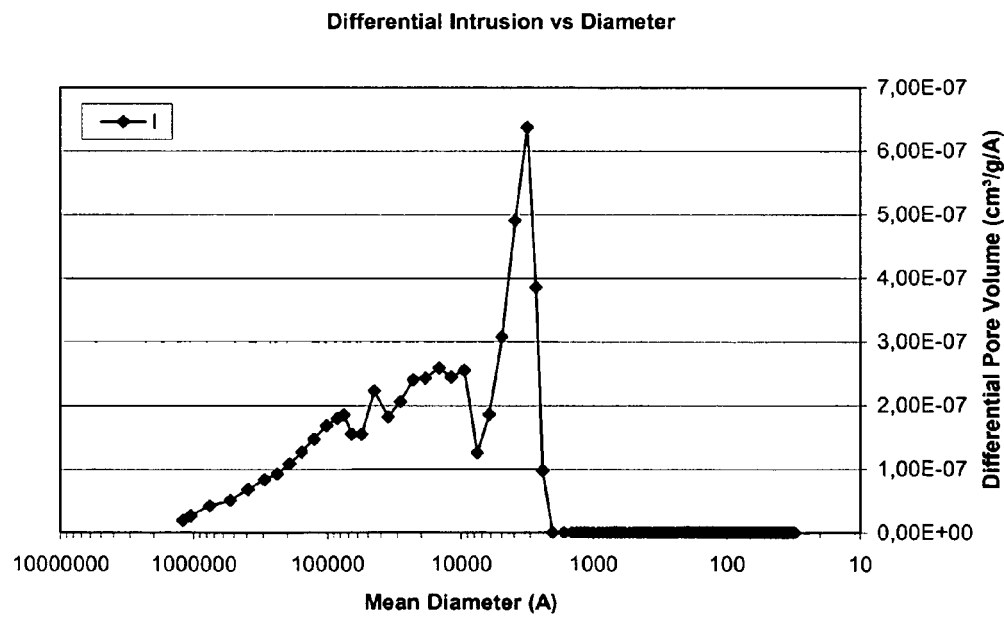
H2 – Differential distribution Fig I1
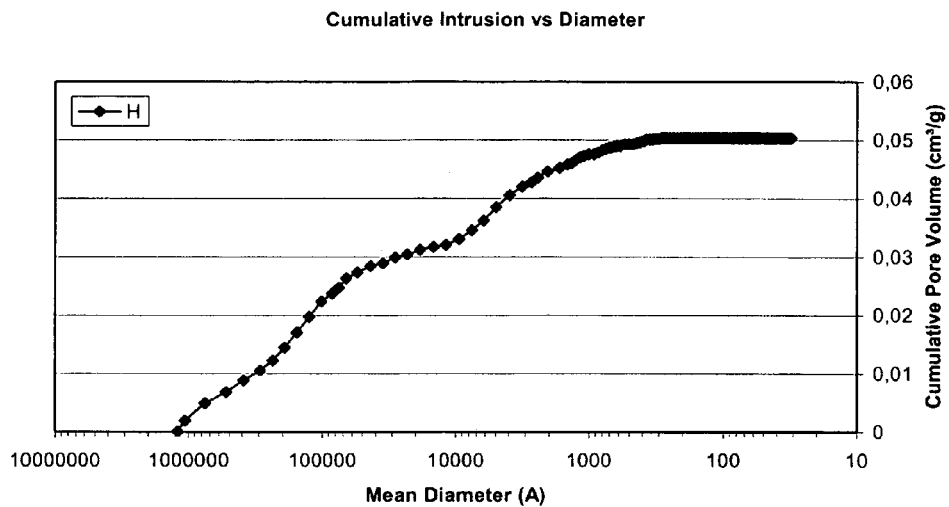
I1 – Cumulative distribution
Fig I2
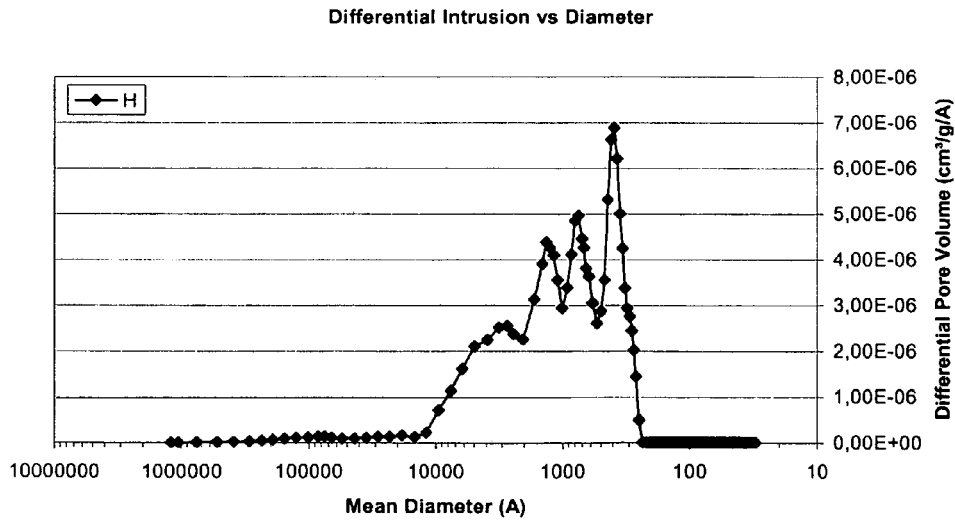
I2 – Differential distribution

POROUS IMPLANT GRAIN OR GRANULE

The present application claims priority under 35 U.S.C. §119(e) to U.S. provisional application Ser. No. 60/902,500 filed Feb. 22, 2007. The present application also claims priority under 35 U.S.C. §365(c), as a continuation-in-part, to PCT Application No. PCT/SE2007/000984 filed Nov. 6 2007. Further, the present application claims priority under 35 U.S.C. §119 to Swedish Application No. 0700457-5 filed Feb. 22, 2007. Each of the above three listed applications are incorporated herein by reference.

FIELD OF THE INVENTION

The present invention relates to an implant, in the form of at least one grain or granule, with anti-inflammatory or antibacterial effects, or both, the implant being intended for implantation in the human or an animal body.

BACKGROUND OF THE INVENTION

It is known that operations and wounds in the body often brings about inflammation and/or infections, which is the case also in connection with implantations, especially in connection with bone tissue, e g hip joints and dental applications.

When titanium is exposed to air or water, an oxide layer is spontaneously formed. This spontaneously formed oxide layer is 4-10 nm thick and consists predominantly of $TiO_2$, Ti(IV), with smaller amounts of Ti(III) and Ti(II) present in the oxide (se references 1, 3 and 4).

The anti-inflammatory and antibacterial effects of titanium are based on the chemical properties of $TiO_2$ at its surface and may work in several different ways, all related to the exposed surface area. As previously shown (reference 2), $TiO_2$ has the ability to directly scavenge ROS (reactive oxygen species). One possible mechanism is through a set of catalytic redox reactions that has been suggested for the breakdown of hydrogen peroxide, superoxide and peroxynitrite on titanium dioxide surfaces (references 2 and 5):

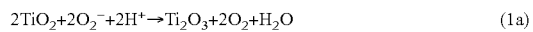

$$2TiO_2 + 2O_2^- + 2H^+ \rightarrow Ti_2O_3 + 2O_2 + H_2O \quad (1a)$$

$$2TiO_2 + H_2O_2 \rightarrow Ti_2O_3 + O_2 + H_2O \quad (1b)$$

$$Ti_2O_3 + OONO^- \rightarrow 2TiO_2 + NO_2^- \quad (2a)$$

$$Ti_2O_3 + H_2O_2 \rightarrow 2TiO_2 + H_2O \quad (2b)$$

Of special interest with respect to the antibacterial effects of titanium is the possibility that $TiO_2$ may also react directly with $H_2O_2$ and form a Ti-peroxy gel, $TiOOH(H_2O)_n$, on the oxide surface. ESR (electron spin resonance) measurements have also shown that superoxide radicals are present in the Ti-peroxy gel, indicating either trapping of superoxide in the gel or direct reaction between superoxide and Ti(IV) in the Ti-peroxy gel (references 5-7). Complexes similar to the Ti-peroxy gel might also be formed between $TiO_2$ and peroxynitrite. It was recently shown that peroxynitrous acid, the protonated form of peroxynitrite ($pK_a$=6.8), forms a complex similar to the Ti-peroxy gel with Ti(IV) under acidic conditions (reference 8). Moreover, the blue tint sometimes found in tissue surrounding titanium implants suggests that Ti(IV) reacts with ROS and forms stable Ti(III) complexes (see reference 9). It has also been shown that the thickness of the titanium oxide layer on implants increases with time in vivo (reference 10), suggesting that Ti metal might act as a sink for oxygen species. All of these reactions might be involved in the direct breakdown of ROS that occurs on the $TiO_2$ surface and the linked anti-inflammatory effect.

Titanium (that is titanium metal with a surface layer of titanium oxide) has been reported to reduce inflammation (Overgaard, Danielsen et al. 1998) and also to be less susceptible to infections than other materials (Johansson, Lindgren et al. 1999). There are also reports describing unique properties of titanium due to its chemical interactions with reactive oxygen species (ROS). The catalytic property of titanium has been shown to be related to the titanium oxide on the surface being present on surfaces composed of only titanium oxide (Sahlin 2006 et al). Such a catalytic property is e.g. described in the US patent application No. 2005074602 to Bjursten et al and also in the generation of titanium peroxy compounds (Tengvall, Elwing et al. 1989; Tengvall, Lundstrom et al. 1989) with anti-inflammatory (Larsson, Persson et al. 2004) and bactericidal properties (Tengvall, Hornsten et al. 1990). The above beneficial properties of titanium seems thus to be linked to its chemical interaction with a living tissue environment.

For references of implants where titanium could be used, U.S. Pat. No. 5,015,256 (Bruce et al) discloses means and a method for fixing an elongate prosthesis, such as the stem of a femoral prosthesis, to living tissue which defines a cavity in which a length of the prosthesis is received with a gap to the boundary of the cavity. Essentially the entire gap is filled with loose, but packed grains of a biocompatible material, said grains interlocking. As an example of granular material titanium is mentioned, and the grains are stated to be irregular, essentially non-elastic and preferably porous, the latter property being said to promote growth of bone tissue which has grown from the osseous wall. The grain interlocking has been achieved by vibrating the stem into a bed of grains housed in said cavity and by a final blow on the stem.

WO00/64504 (Bruce et al) discloses a biocompatible, plastic or essentially non-elastic, porous body, such as a grain, with continuous porosity, the openings of cavities and the passages interconnecting them having a width of >about 50 µm for bone tissue. The term "continuous" is said to mean a porosity which allows bone tissue to grow through the porous body. The porous body may be of titanium.

One disadvantage with the inventions according to U.S. Pat. No. 5,015,256 and WO00/64504 is the fact that the grains according to these inventions are not optimised for anti-inflammatory and/or antibacterial effects. In fact, U.S. Pat. No. 5,015,256 and WO00/64504 do not disclose anything about any possible anti-inflammatory and/or antibacterial effects.

The present invention aims at solving this problem by providing a modified grain or granule with enhanced anti-inflammatory and/or antibacterial effect.

SUMMARY OF THE INVENTION

One object of the present invention is thus to provide an implant, such as a grain or granule, with very high specific surface area and hence enhanced antibacterial, anti-inflammatory effects in relation to titanium grains and bodies according to state of the art.

This object is achieved by an implant with anti-inflammatory or antibacterial effects, or both, the implant being intended for implantation in a human or an animal body, the implant comprising at least one porous grain or granule, wherein the at least one porous grain or granule comprises titanium, one or more titanium oxides or titanium alloy and has a titanium oxide layer on its surface;

has a mean length from one side to the opposite side, through a geometrical centre, of up to 5 mm;

has a mean specific surface area of at least 0.15 m²/g according to the BET method.

Below, the BET method will be explained in more detail, but another method for more simplified calculation of the specific surface area, which method was used in the experiments as well, will be explained first.

Methods Used for Evaluation of Mean Pore Volume, Mean Pore Diameter and Specific Surface Area Mercury Intrusion Porosimetry A nonwetting liquid like mercury (Hg) does not spontaneously fill pores of a sample because the sample/nonwetting liquid surface free energy is greater than the sample/gas surface free energy. However, application of pressure can force a nonwetting liquid into the pores of a sample, the differential pressure required to force a nonwetting liquid into a pore is given by $$P = -4\gamma \cos \theta / D,$$

where
P=differential pressure
γ=surface tension of nonwetting liquid
θ=contact angle of the nonwetting liquid with the sample
D=pore diameter As pressure on the filled penetrometer increases, mercury intrudes into the pores of the sample, beginning with those pores of largest diameter. This requires that mercury move from the capillary stem into the cup, resulting in a decreased capacitance between the now shorter mercury column inside the stem and the metal cladding on the outer surface of the stem.

Penetrometers are available for both solid as well as powder specimens. There is also a wide selection of both cup and stem volumes. In this way it is possible to optimise the output of the analysis.

According to the present invention the pore volume and pore size distribution have been measured on different grains according to the invention (see example 1 and tables 1 and 2). The measurements where performed with a mercury porosimeter (Micromeritics AutoPore III 9410) in the range of 150 μm≥pore size diameter≥0.003 μm (30 Å). The surface tension of the mercury was set at 485 mN/m and the contact angle, θ, to 130°. This method is referred to as the Hg method in the summary of the present invention above, as well as hereinafter.

Surface Area by Gas Adsorption

Surface area by gas adsorption is a measure of the exposed surface of a material reported in terms of square meters per gram. This most common model for assessing surface area is referred to as BET (Brunauer, Emmet and Teller) surface area or simply BET number. The key to obtaining a reliable, repeatable surface area result is to prepare the sample properly. Samples are prepared or degassed by applying some combination of heat, vacuum and/or flowing gas. This removes previously adsorbed contaminants from the surface and from the pores. Failure to remove these components effectively can result in erroneous data. The sample then is cooled to cryogenic temperature, and an adsorptive gas (typically $N_2$) is admitted to the sample tube in controlled increments. After each dose, the pressure is allowed to equilibrate, and the quantity of gas adsorbed is calculated. The gas volume adsorbed at each pressure defines an adsorption isotherm. The quantity of gas required to form a monolayer over the surface of the solid is determined from the isotherm. The external surface area or BET surface area can be determined from the area covered by each adsorbed gas molecule known and the monolayer capacity known.

Firstly, isolated sites on the sample surface begin to adsorb gas molecules. Secondly, as gas pressure increases, coverage of gas molecules increases to form a monolayer. BET equation is used to calculate the surface area in this secondary stage. Thirdly, increasing gas pressure causes multilayer coverage. Smaller pores fill first. Still higher pressure then causes complete coverage of the sample and fill all of the pores. Pore diameter, volume and distribution calculation can be made by using the BJH (Barrett, Joyner, Halenda) method for surface calculation.

In multiple point equipment, the secondary stage as well as the final stage both are used for determination of the pore size distribution.

The Gemini Principle and Instrumentation

The Gemini uses an adaptive rate, static volumetric technique of operation. It is the first gas sorption method, which adapts the required rate at which gas is supplied for equilibration. The Gemini has two gas reservoirs, which are filled with equal volumes of the desired adsorptive, usually nitrogen. From the reservoirs, gas is dosed into the sample and balance tubes. A transducer on the sample side monitors for the target pressure. As the sample adsorbs gas, the pressure would tend to decrease in the sample tube was it not that a first transducer causes a fast response servo valve to hold the pressure constant. A second transducer located between the sample and balance tubes detects any pressure difference between the two tubes and causes another servo valve to balance the pressures in both tubes. A third pressure transducer monitors the pressure between the two reservoirs to determine the amount of gas that is adsorbed on the sample. This method of dosing and accounting for the volume of gas uptake enables the Gemini to produce highly accurate, highly reproducible results in the minimum time.

According to the present invention the specific surface area has been measured on different grains according to the invention according to the BET method, by using multiple point determination (Micromeritics Gemini 2360) (see example 1 and tables 1 and 2).

The determination of specific surface area according to this method is in the summary above as well as hereinafter described as determination according to the BET method.

The reason why both of the different methods for determining the specific surface area have been used is due to comparison reasons. The two methods do not correlate perfectly to one another, but the BET method should be considered as the more accurate one in relation to the absolute value of the specific surface area. The reasons of differences of the methods are described in example 1 below.

BRIEF DESCRIPTION OF THE DRAWINGS

In drawing 1, FIGS. A1 and A2 show the cumulative intrusion vs. pore diameter and differential intrusion vs. pore diameter, respectively. FIG. A1 is a graph of the relationship between the cumulative pore volume (cm³/g) and mean pore diameter (Ångström (A)) for grain sample A according to the invention. FIG. A2 is a graph of the relationship between the differential pore volume (cm³/g) and mean pore diameter (Ångström (A)) for grain sample A according to the invention.

In drawing 2, FIGS. B1 and B2 show the cumulative intrusion vs. pore diameter and differential intrusion vs. pore diameter, respectively. FIG. B1 is a graph of the relationship between the cumulative pore volume (cm³/g) and mean pore diameter (Ångström (A)) for grain sample B according to the invention. FIG. B2 is a graph of the relationship between the differential pore volume (cm³/g) and mean pore diameter (Ångström (A)) for grain sample B according to the invention.

The FIG. C1 to I1 and C2 to I2 of drawings 3 to 6 and 8 to 10 also show the cumulative intrusion vs. pore diameter and differential intrusion vs. pore diameter for different samples in the same way as drawings 1 and 2. All of them are grain samples according to the invention except for sample G (drawing 8, FIGS. G1 and G2), which is a sample of a grain which is commercial available and referred hereinafter to as start material 2.

FIG. F3, drawing 7, show the incremental intrusion vs. pore diameter for grain sample F. FIG. F3 is a graph of the relationship between the incremental pore volume (cm³/g) and mean pore diameter (Ångström (A)) for grain sample F according to the invention.

DETAILED DESCRIPTION OF THE INVENTION

As mentioned above, it is known that titanium has beneficial properties in relation to reduction of inflammation. However, it is not known how to provide a grain or granule with enhanced anti-inflammatory and/or antibacterial effects.

There are a couple of important factors for achieving a grain or granule with enhanced anti-inflammatory and/or antibacterial effects. One of these factors or parameters is a high specific surface area of the grains or granules. Firstly, the size or diameter of the grain or granule affects the specific surface area, where the specific surface area for a perfect sphere decreases proportionally with the increase of the diameter, i.e. a 10 times increase of the original diameter decreases the specific surface area to ¹/₁₀ of the original specific surface area. This means that smaller grains or granules have a higher surface area than larger ones. However, porosity is of great importance for higher specific surface area, and really small grains, that is particles, can not be porous. As many cavities or pores possible are to be comprised in a granule or sponge to achieve the highest possible specific surface area. With two identical grains in size, the one of them having many small pores has a larger specific surface area but smaller total pore volume in comparison to the other one with larger pores.

Thirdly, the irregularity is important. An irregular body has a higher specific surface area than a smooth body. As such, and in the two most opposite cases, an irregular flake of the same weight as a perfect smooth sphere has a much higher specific surface area than the sphere. Therefore, the grains or granules according to the present invention are preferably irregular, both in relation to surface of the grains or granules as well as the surface of the pores of these grains or granules.

As is mentioned, there is a focus on the surface of the grains or granules which is due to the fact that many chemical reactions are dependent on the characteristics on the surface.

When stating the implant according to the invention as at least one grain or granule, it is important to understand the differences between the implants according to the present invention and "whole-body implants" according to state of the art. These "whole-body implants" are e.g. a titanium screw or a tooth, and not at all grains or granules, and common for all of these "whole-body implants" are that they have at least one fastening or fixing element, which is not the case with grains or granules according to the present invention.

In an effort to take advantage of the beneficial properties of titanium as much as possible as well as produce a grain or granule with extremely high surface area, the inventors investigated crude spongy titanium from different suppliers, regarding e.g. their porosity. These investigations showed that crude titanium sponge produced by the well-known Hunter process or Kroll process is potentially a good candidate as crude material for forming an implant body (grain or granule) with such aimed properties, that is property to allow growth and ingrowth of tissue (bone; bone regeneration) as well as a property to have a bactericidal and anti-inflammatory effect, when placed in living tissue.

Other existing techniques suitable to use when producing the crude titanium/titanium alloy material, that is as sponges or blocks, are e.g. a direct foaming technique as gel casting, or other wet processing methods as a replication technique and a rapid prototyping technique.

The value of the specific surface area of grains or granules of titanium oxide/oxides, titanium or titanium alloy according to the invention has proven to be an direct indication on the anti-inflammatory or antibacterial effects of the titanium or titanium alloy grain or granule.

The inventors found out that bodies of titanium sponge have a far better antibacterial and anti-inflammatory effect than bodies of non-porous titanium, which made them understand that effective surface area of a titanium body is a very important determining factor for good anti-bacterial and anti-inflammatory effect of titanium implants.

Both a sponge and small particles according to the invention can possess antibacterial and anti-inflammatory effects. This proves that porosity is not the only determining factor for these effects, but size as well as irregularity are important as well. As mentioned, all of these three parameters determine the specific surface area, which is a measurement in direct correlation with the antibacterial and anti-inflammatory effects of an implant according to the invention. In other words, this measurement is a feature of great importance for characterising the implant according to the invention.

However, it has turned out that increasing the surface area of a titanium implant by disintegrating (crushing) it to smaller pieces does not consistently bring about an improved antibacterial/anti-inflammatory effect.

Still further, the inventors have surprisingly found that not only the size and the specific surface area of the titanium or titanium alloy body are determining for antibacterial and anti-inflammatory effects but also other factors and conditions presented below are of great interest. For example could these effects be enhanced by binding or attaching other substances with specific properties to the implant according to the invention.

To summarise, the implant according to the invention possesses enhanced antibacterial and anti-inflammatory effects which are related to its specific features in terms of size, irregularity and porosity, which all determine the value of the specific surface area of the implant.

To achieve these beneficial effects there is according to the invention provided an implant with anti-inflammatory or anti-bacterial effects, or both, the implant being intended for implantation in a human or an animal body, the implant comprising at least one porous grain or granule, wherein the at least one porous grain or granule comprises titanium, one or more titanium oxides or titanium alloy and has a titanium oxide layer on its surface;

has a mean length from one side to the opposite side, through a geometrical centre, of up to 5 mm;

has a mean specific surface area of at least 0.15 m²/g according to the BET method.

In this application the expression "implant" has the form of a single piece body, including one grain or granule or an agglomerate of particles and/or grains, bonded together or not. Different expressions for the implant are used through out the description. Examples meaning the same thing are the expressions "granule" and "grain".

The inventors have found that for achieving effective antibacterial and anti-inflammatory effects, the implant must have a mean length from one side to the opposite side, through a geometrical centre, (referred to as the diameter in some cases) of maximum up to 5 mm, preferably from 200 μm and up to 2 mm. Therefore, according to one preferred embodiment of the present invention, the at least one porous grain or granule of the implant has a mean "diameter" of at least 200 μm and up to 2 mm. This is also applicable for an agglomerate of more than one grain or granule, where the grains are bonded together or not.

The implants of the invention however have an irregular shape, and with diameter is meant the longest axis length of two opposite points on a cross section of the implant. It is important to understand that the grains or granules do not have to have the shape of a sphere. In fact, the irregularity of the implants is an important feature, and shapes that are more irregular, such as e.g. flakes, spikes, chips or similar or combinations thereof are preferred.

The inventors have found that it is not any point to decrease the diameter of the implant below 5 μm to increase the anti-inflammatory/antibacterial effect, while below such a diameter the titanium implant is phagocytized, i.e. "eaten up" by the macrophages, whereby the anti-inflammatory/antibacterial effect of the titanium implant is destroyed. Moreover, implants >5 mm are not realistic to use in applications according to the invention, that is for implantation in a human/animal body, such as e.g. in dental applications. That is also why implants with a size or diameter of from at least 200 μm and up to 2 mm is the most applicable.

There exist possible ways to enhance the desired structure of the granule in relation to irregularity, enhanced porosity and specific surface area. This is possible to perform by etching or roughening, where these two methods sometimes are used in combination. One feature distinguishing the implant is as mentioned the irregular shape, and hence, roughening can be an aid to form or enhance this irregular shape of the implant.

There exist different types of chemicals which can be used for etching. Some of them have additional beneficial effects to enhance the anti-inflammatory and/or antibacterial effects. One example is peroxides, e.g. a hydrogen peroxide solution.

The reaction product of hydrogen peroxide and metallic titanium, that is a titanium peroxy radical gel, is disclosed as an anti-inflammatory oxidizing agent in the international patent publication WO89/06548 (Bjursten et al.). WO89/06548 discloses the reaction gel product as a coating on implants made of titanium or with a titanium coating, but these implants are not in any way similar to the implant according to the present invention. The implants according to WO89/06548, however, are not grains or granules as the case in the present invention, but solid implants for a specific function, as e.g. a titanium screw. In other words, an implant according to WO89/06548 could be categorized as a "whole-body prosthesis".

The surface, including the pore surfaces, of the implant according to the invention may be exposed to peroxides, as mentioned, before the implant is implanted, whereby the antibacterial effect of the implant is enhanced.

There exist other chemicals which could be used for similar purposes, that is etching and enhancing the anti-inflammatory and/or antibacterial effects.

Therefore, according to one embodiment of the present invention there is provided an implant, wherein the at least one porous grain or granule has been treated with at least one fluoric compound, fluoride acids, hydrochloric acid, sulphuric acid, phosphorous acid, a peroxide compound chosen from the group consisting of hydrogen peroxide ($H_2O_2$) and organic peroxides, or oxalic acid, or a combination thereof, or has been dry etched with fluorinated or chlorinated gases. This treatment is made to enhance the specific surface area of the at least one porous grain or granule and/or to oxidise the at least one porous grain or granule.

According to one specific embodiment of the invention, the fluoric compound used in the treatment is any type of fluoric acid, hydrofluoric acid in combination with nitric acid, ammonium fluoride, ammonium bifluoride (also in combination with nitric acid), or hydrogen fluoride (HF).

The treatment conditions vary in relation to concentration, time and temperature, depending on the specific chemical used as well, and there are many different combinations possible to use. There are specific examples provided in example 1 below, but these should be interpreted as examples and not as a limitation of the scope of the present invention.

According to one specific embodiment, the concentration of the chemical used in the treatment above is from 0.05 to 1.0% for fluoride acids, from 0.5 to 30.0% for hydrogen peroxides and from 0.2 to 20.0% for oxalic acids. According to one specific example, the concentration is about 0.2% for fluoride acids, about 30% for hydrogen peroxides and about 10% for oxalic acids.

Oxidation is also an effective method for changing the chemistry of the grain. Oxidation could be used for different purposes, e.g. for increasing the specific surface area of the grain, for enhancing the amount of titanium oxide and thereby the possible antibacterial and/or anti-inflammatory effect or for altering the appearance of the grain, or a combination thereof.

According to one embodiment of the present invention, the at least one porous grain or granule has been oxidised by heat treatment in oxidising atmosphere at temperatures between 20 and 1000° C. and/or by electrochemical procedure.

According to another specific embodiment, the at least one porous grain or granule has been anodically oxidized using spark erosion to increase the surface area.

According to yet another embodiment of the present invention, the at least one porous grain or granule has been produced according to a spark erosion procedure where the at least one porous grain or granule has been brought into contact with an anode using a flexible net or porous sponge-like structure.

Anodic spark deposition of titanium or titanium alloy implants is e.g. described in "Osteointegration of titanium and its alloys by anodic spark deposition and other electrochemical techniques: A review" in Journal of Applied Biomaterials & Biomechanics 2003; 1: 91-107 by R. Chiesa et al. The deposition according to the document above was achieved by potentiostatic polarization of the cathode with a potential in the range of −1 500 to −1 300 mV (vs. SCE). The implants described in this document are homogenous implants with surface modified by spark deposition and thus fundamentally different from the grains or granules according to the present invention.

According to one specific embodiment of the present invention, the at least one porous grain or granule is provided with nanotubes of titanium oxide, by a pre-treatment involving anodic oxidation, on its surface. This pre-treatment comprising anodic oxidation can e.g. be performed according to Cai, Paulose, et al. in "The effect of electrolyte composition on the fabrication of self-organized titanium oxide nanotube arrays by anodic oxidation", J Mater Res 2005 20; 1:230-6, or according to Macak, Tsuchiya et al. in "Smooth Anodic $TiO_2$ Nanotubes", Angewandte Chemie: a journal of the Gesellschaft Deutscher Chemiker, Int. ed. 44; 2005; 7463-65, which both in full are hereby incorporated by reference.

The provision of nanotubes of titanium oxide on the surface of the at least one porous grain or granule according to the present invention may be of importance to achieve an extra high specific surface area and hence a surface which are highly bone inducting. Furthermore, the application of nanotubes of titanium oxide is possible to perform on solid grains or granules to be able to achieve porous grains or granules according to the present invention comprising titanium, one or more titanium oxides or titanium alloy and having a mean specific surface area of at least 0.15 $m^2$/g according to the BET method. This large specific surface area may be achieved on solid grains or granules by either a surface treatment, e.g. with hydrogen peroxide as is described, or by providing nanotubes on their surface, both ways making the grains or granules porous on their surfaces. This implies that the porosity according to the present invention does not have to be continuous, that is pores extending through the grains or granules, but the pores may instead be provided only on the surfaces of the grains or granules according to the present invention.

As mentioned in the references above it is possible to produce nanotubes with a length of up to 7 μm using the specific conditions disclosed in those references. Therefore, it should, by use of some modifications, be possible to produce nanotubes with an individual length of up to about 10 μm. In any case, nanotubes of a length of 1-5 μm are without specific optimisation possible to achieve, and hence possible to provide on the surfaces of the grains or granules according to the present invention by anodic oxidation. Nanotubes of a length of up to about 1 μm have good mechanical properties, so this length is quite sufficient in relation to this embodiment of the present invention.

Anodic oxidation is performed in some kind of electrolyte. Hydrofluoric acid (HF) is a component which is often comprised in the electrolyte. However, if the length of the produced nanotubes is of great importance, e.g. electrolyte solutions containing potassium fluoride, sodium fluoride, glycerol, $(NH_4)_2SO_4$ or $(NH_4)F$ may be suitably used for production of longer nanotubes of titanium oxide. Therefore, according to one specific embodiment of the present invention the at least one porous grain or granule is provided with nanotubes of titanium oxide, by a pre-treatment involving anodic oxidation, on its surface, in an electrolyte solution comprising hydrofluoric acid (HF), potassium fluoride (KF), sodium fluoride (NaF), glycerol, $(NH_4)_2SO_4$ or $(NH_4)F$ or a combination thereof. The electrolyte solutions may of course contain other chemicals as well and these may be added for different reasons. For example, pH adjustment of the electrolyte solutions may be performed by the addition of e.g. sulphuric acid, sodium hydroxide, sodium hydrogen sulphate, citric acid, among others.

One example on how to provide nanotubes on the surface of the at least one porous grain or granule according to present invention is by use of electrodes which are designed as a tea bag or a net of noble metal, e.g. of platinum, which bag or net has a mesh size which is smaller than the diameters or sizes of the grains or granules so that these grains or granules are held inside of the bag or net. Once again, one example of a suitable electrolyte is an electrolyte solution comprising hydrofluoric acid (HF), potassium fluoride (KF), sodium fluoride (NaF), glycerol, $(NH_4)_2SO_4$ or $(NH_4)F$ or a combination thereof.

According to the present invention, as mentioned above, it is possible to alter the appearance of the grain or granule according to the invention by oxidation. According to one specific embodiment of the present invention, the at least one porous grain or granule is heat treated in inert atmosphere or vacuum at a temperature of 500° C. or above, but below the melting point of the titanium, one or more titanium oxides or the titanium alloy. The normal colour of the grains are greyish, but in some cases, as dental applications, it could be advantageous to alter this colour and achieve a more yellowish and/or whitish appearance. Thus, this is achieved by an oxidation where the thickness of the formed titanium oxide layer is of great importance. This thickness should substantially be at least 500 nm, which has to do with the wavelength of light, where the visible light has a wavelength of 400-700 nm. According to one specific embodiment of the present invention such an implant of at least one yellowish and/or whitish porous grain or granule is provided at least partially with an outer layer of titanium or titanium alloy having a thickness in the range of 30-500 nm. The latter is sometimes preferred to provide the chemical properties of the titanium or titanium alloy to the implant while still keeping the yellowish and/or whitish appearance. Such a thin outer metal layer is possible to provide by CVD (chemical vapour deposition) without risking to fill the pores and hence decrease the porosity.

It has previously been found that the crystalline isoforms, anatase and rutile, of titanium oxide are more efficient than the amorphous titanium oxide in the catalytic reactions described in this patent application above, as the source of the anti-inflammatory and bactericidal properties of titanium. Thus, with the use of quantitative photon counting microscopy, the inventors were able to measure the chemiluminescent signal from MCLA (2-methyl-6-[p-methoxyphenyl]-3, 7-dihydroimidazo[1,2-a]pyrazin-3-one) induced by production of superoxide from J774A.1 mouse macrophages stimulated with PMA (phorbol 12-myristate 13-acetate) and found a significant reduction by the crystalline phases.

In order to increase the efficiency of the porous titanium granules they may be transformed into the crystalline isoforms by heat treatment in inert atmosphere or vacuum. It is known that such transformation occurs at temperatures above 900° C. (reference 11), but well below the melting point of titanium (1668° C.) and in some instances as low as 500° C.

Therefore, according to one embodiment of the present invention, the at least one porous grain or granule has been heat treated in inert atmosphere or vacuum at a temperature of 500° C. or above, but below the melting point of the titanium, one or more titanium oxides or the titanium alloy.

As mentioned before, the value of the specific surface area of the grain according to the invention is of great importance for the anti-inflammatory and/or antibacterial effects, and could be regarded as a direct indication on the magnitude of these effects. However, as discussed above, there are other important factors as well for these effects. As disclosed in the examples below, there are different levels of specific surface area obtainable by different treatments of the grains or granules according to the invention.

According to one embodiment of the present invention the at least one porous grain or granule has been treated with HF or $H_2O_2$ and has a mean specific surface area of at least 0.25 $m^2$/g according to the BET method.

According to another specific embodiment of the present invention the at least one porous grain or granule has been treated with HF and has a mean specific surface area of at least 0.40 $m^2$/g according to the BET method.

According to yet another specific embodiment of the present invention the at least one porous grain or granule has been oxidised and has a mean specific surface area of at least 0.40 $m^2$/g according to the BET method.

Another object of the invention is to still improve the properties of an implant according to the invention by treating it with other possibly beneficial substances to increase the antibacterial and anti-inflammatory effects of the implant.

Additional advantageous effects may be obtained by addition of substances that influence the biological environment. This could be achieved by filling or incorporating the porous bodies, i.e. the grains, according to the invention with such substances or combinations thereof or by modification of the surface of the grains or the outer surface or the pores of the grains. This could for example be achieved by binding or attaching at least one substance to the surface of the grains or to the surface of or into the pores of the grains. By other modifications, including binding of biologically active substances, the implant may enhance tissue healing, remodelling or ingrowth.

Therefore, according to one embodiment of the present invention, at least one substance, which substance is biologically active, is filled into the pores of the at least one porous grain or granule and/or is bound to the surface of the at least one porous grain or granule.

These additional substances may e.g. be factors promoting tissue growth or regeneration, or be antibiotics. Therefore, according to one embodiment of the present invention, the at least one substance is chosen from the group of antibiotics, factors promoting tissue growth or regeneration, anti-inflammatory oxidizing agents or a combination thereof. Examples of such sub-stances or factors are bone morphogenic factor, andronate, alfa-keto glutarate, simvastatin, Emdogain® (see below), gentamicin and synthetic type I collagen (as PepGen P-15). Another example is peroxides, e.g. a hydrogen peroxide solution, which already has been mentioned.

As is disclosed in patent US 2005/0214231 A1, which content hereby in full is incorporated by reference, enamel matrix, enamel matrix derivatives or enamel matrix proteins (collectively termed "active enamel substance" in the following) are able to induce dentin formation in dental pulps. Some of these active enamel substances or pharmaceutical compositions thereof are also substances and compositions which are suitable to fill, attach or bind to the implant according to the invention. This is performed in some dental applications to achieve an enhanced anti-inflammatory and/or antibacterial effect and to achieve synergic effects of the good properties of the implant in itself and the enamel substance or composition thereof in itself. In some of the cases there is also other positive effects achieved by the combination of the implant and an active enamel substance or a pharmaceutical composition thereof, e.g. a stronger and more stable fixing of e.g. a titanium screw with the human or animal tissue around the cavity in which the titanium screw is to be fixated. This could in other words be beneficial for dental applications wherein a cavity is filled with these "active enamel substance filled" grain implants according to the invention.

Enamel matrix is a precursor to enamel and may be obtained from any relevant natural source, i.e. a mammal in which teeth are under development. A suitable source is developing teeth from slaughtered animals such as, e.g., calves, pigs, or lambs. Another source is for example fish skin.

In the present context, enamel matrix derivatives are derivatives of enamel matrix which include one or several enamel matrix proteins or parts of such proteins, produced naturally by alternate splicing or processing, or by either enzymatic or chemical cleavage of a natural length protein, or by synthesis of polypeptides in vitro or in vivo (recombinant DNA methods or cultivation of diploid cells). Enamel matrix proteins derivatives also include enamel matrix related polypeptides or proteins. The polypeptides or proteins may be bound to a suitable biodegradable carrier molecule, such as polyamino acids or polysaccharides, or combinations thereof. Furthermore, the term enamel matrix derivatives also encompasses synthetic analogous substances.

According to one embodiment of the present invention, the at least one substance, which is filled into the pores of the at least one porous grain or granule and/or is bound to the surface of the at least one porous grain or granule, is at least one active enamel substance, which active enamel substance is enamel matrix, enamel matrix derivatives or enamel matrix proteins or combinations thereof.

Enamel matrix proteins are proteins which normally are present in enamel matrix, i.e. the precursor for enamel (Ten Cate: Oral Histology, 1994; Robinson: Eur. J. Oral Science, January 1998, 106 Suppl. 1:282-91), or proteins which can be obtained by cleavage of such proteins. In general such proteins have a molecular weight below 120 000 daltons and include amelogenins, non-amelogenins, proline-rich non-amelogenins, amelins (ameloblastin, sheathlin, tuftelins, dentinsialoprotein (DSP) or dentinsialophosphoprotein (DSPP). Examples of proteins are amelogenins, proline-rich non-amelogenins, tuftelin, tuft proteins, serum proteins, salivary proteins, amelin, ameloblastin, sheathlin, and derivatives thereof, and mixtures thereof. A preparation containing an active enamel substance for use according to the invention may also contain at least two of the aforementioned proteinaceous substances.

According to one embodiment of the present invention, the at least one active enamel substance is selected from the group consisting of enameling, amelogenins, non-amelogenins, proline-rich nonamelogenins, amelins (ameloblastin, sheathlin), tuftelins, tuft proteins, salivary proteins, DSP, DSPP, and derivatives thereof and combinations and mixtures thereof.

Emdogain®, which is mentioned above, is a commercial product comprising amelogenins. Emdogain® is marketed by Biora AB and it comprises about 30 mg/ml of active enamel substance in propylene glycol alginate (PGA). This is a preferred amount in a possible pharmaceutical composition for incorporating, filling, attaching or binding to the implant according to the invention.

Therefore, according to one embodiment of the invention, the at least one substance is one active enamel substance that is mixed with propylene glycole alginate (PGA).

The implant comprising grains or granules according to the invention is also possibly admixed with fluid vehicles. Therefore, according to one embodiment of the present invention, the implant is additional admixed with at least one fluid vehicle, the fluid vehicle e.g. being NaCl (aq), hyaluronic acid, PEG, propylene glycole alginate (PGA), titanium peroxy gel, methyl cellulose, carbomethyl cellulose, dextran, a high viscous polymeric gel, or a protein solution, or a combination thereof.

According to another embodiment of the present invention, the at least one fluid vehicle is comprised in a gel having a melting temperature above ambient temperature and below 37° C. (body temperature), which gel optionally comprises at least one of NaCl (aq), hyaluronic acid, PEG, propylene glycole alginate (PGA), titanium peroxy gel, methyl cellulose, carbomethyl cellulose, dextran, a high viscous polymeric gel, or a protein solution. This gel may be particularly useful in view of the fact that the gel and its containing grains or granules and optionally smaller particles will be easy to e.g. inject into a human or animal body when it is in a gel solid state at ambient temperature, but at the same time the gel becomes liquid at a normal body temperature making it readily and rapidly resorbable. Examples of such gels having that range of melting temperature may e.g. comprise hyaluronic acid in the right concentration for that gel to dissolve when being injected into a human or animal body.

There are different ways of binding substances to the grains, or modify the grains, according to the invention. The physical and chemical surface modification methods can be categorized into three different types, the noncovalent coatings, the covalently attached coatings and modifications of the original surface.

The methods used for noncovalent coatings are preferably solvent coatings, surface-active additives or vapor deposition of carbons and metals, in which the latter one some covalent reaction may occur.

The preferred methods for covalently attached coatings are RFGD plasma deposition, in this case at low-pressure ionized gas environments typically at about ambient temperature, other plasma gas processes, gas-phase deposition, as chemical vapour deposition (CVD), chemical grafting and biological modification (biomolecule immobilization).

The methods for modifications of the original surface are preferably ion exchange, by chemical reactions, like non-specific oxidation, and conversion coatings.

It should be noted that the implant according to the invention possibly comprises several grains or granules, attached to one another or not. Therefore, according to one embodiment of the present invention, the at least one porous grain or granule is an individual in an aggregate of similar grains or granules.

Addition of factors that increase the initial adherence of the granules to each other and to the surrounding tissue may also be added. These should preferably be resorbable, an example of this is fibrin. Other possibilities are to use synthetic adhesives like cyanoacrylate.

It should also be noted that a minor fraction of the implant according to the invention may be of other material than titanium, one or more titanium oxides or titanium alloy, e g allogenic bone, ceramics, polymers, adhesives.

An object of the present invention is also to provide methods for treatment of conditions comprising an inflammation or/and an infection present in a human or animal body.

According to one embodiment of the present invention, there is provided a method for treating a condition comprising an inflammation or/and an infection present in a human or animal body, wherein an implant according to the invention is brought into contact with an inflamed/infected site in the human or animal body. Different possible conditions are e.g. periodontitis, periimplantitis and osteitis. The implants according to the present invention may also be of interest to inject into or insert to non-inflamed and/or non-infected sites of a human or animal body for different reasons, e.g. into specific parts or organs of a human or animal body in vivo or in vitro. Such parts or organs may e.g. be the intestine, liver, spleen, pancreas or e.g. the kidneys. One example of use of the grains or granules is as a carrier of medicaments to specific parts of the human or animal body, where the grains or granules either work just as a carrier or as an active medicament in combination with the other medicaments at the site intended to be contacted.

According to another embodiment of the present invention, there is provided a method for treating a condition according to above, wherein the implant according to the present invention is additionally treated in vivo by UV radiation with a wavelength $\lambda$ of 200-500 nm. This is sometimes desirable due to the fact that it is hence possible to enhance the anti-inflammatory and/or antibacterial effect, as the UV radiation generates radicals. One specific example of a suitable wavelength range of the UV radiation is 250-350 nm.

There may exist other factors of interest for methods of treatment of conditions as above, where an implant according to the present invention is brought into contact with an inflamed/infected site in the human or animal body. One such factor could in some cases be the importance of immobility and stability of the implant in a specific cavity, e.g. a dental cavity, when this cavity is to be treated for its infection. The infections and inflammatory processes to be treated are often located in cavities that are naturally formed or a result of the disease process. The cavity may also be created by taking out a part of an inflamed/infected tissue. In these cases it may be important to secure the implant in the described cavity. This is possible to achieve by different methods, e.g. designing the implant as a single body in one piece which is designed to fill out the cavity with a close fit, or by using adhesive, non-inflammatory and non-bacterial, preferably anti-inflammatory and antibacterial substances.

However, there could be places in the body which are infected where the supply of the implants is made without any creation of a cavity. One example is if there is a infection or inflammation in the intestine. In this case it is of course as well important that the implant is brought into contact with the infected site of the e.g. intestine.

According to the present invention there is also provided an implant according to the invention, for use as a medicament. This medicament is effective to use for the treatment of a condition comprising an inflammation or/and an infection present in a human or animal body. This medicament may, furthermore, according to the invention comprise the at least one grain or granule of the implant as such, an agglomerate of several grains or granules or a kit of this grain, grains or agglomerate as well as a substance according to what is described above. Other possible substances in such a kit may be a sterile solution, e.g. of NaCl (aq), cell nutrients, growth factors or other proteins, peptides or salts.

The implant according to the invention may also used for the manufacture of a medicament, e.g. a kit, for the treatment of a condition comprising an inflammation or/and an infection present in a human or animal body. Examples of conditions are e.g. periodontitis, periimplantitis or osteitis.

Finally, with the present invention, there is provided a method for producing implants according to the invention from a piece of a crude titanium or titanium alloy sponge, the method comprising the steps of:

choosing and removing a porous peripheral, but not most outer, part of the piece of the crude titanium or titanium alloy sponge;

analysing that part in view of the chemical composition for potential impurities;

crushing that part, if pure, and;

finally selecting the implants by sieving and analysis in batches, the analysis in batches being performed by scanning electron microscopy (SEM) or by gas absorption with nitrogen, the Hg method and/or the BET method.

According to the invention, the term "crude" titanium or titanium alloy means the start material, produced e.g. by the Hunter process or Kroll process, from which start or crude material the implants according to the invention are produced. Suitable crude titanium sponge for making implants according to the invention is marketed as "Alfa Aesar" (Johnson Matthey), USA, Product No. 042459.

EXAMPLES AND DETAILED DESCRIPTION OF THE DRAWINGS

Example 1

Determination of the Specific Surface Area of an Implant Grain or Granule According to the Invention The inventors measured the specific surface area of an implant according to the invention, the possible increase of the specific surface area when treating an implant according to the invention, and compared the results with the specific surface area of start material and a commercially available grain.

The measurement methods used was the Hg method and BET method disclosed above in the section "Methods used for evaluation of mean pore volume, mean pore diameter and specific surface area". Both methods was used because of comparison reasons.

The diameters of the grains or granules used were in the range of 0.7-1.4 mm.

The pore volume and the pore size (diameter) distribution for grain samples A to I was determined by a mercury porosimeter (Micromeritics AutoPore III 9410) in the range of 150 μm≥pore size diameter≥0.003 μm (30 Å). The surface tension of the mercury were set at 485 mN/m and the contact angle, θ, to 130°. Correction for compression of parts of the sample holder at high pressures was made (see blank correction in FIG. 1 to 10). This was not made for grain samples H and I due to the fact that these were analysed with a sample holder which is not compressed at high pressures.

Specific surface area for grain samples A, D to I has been measured according to the BET method, multiple point determination (Micromeritics Gemini 2360). This was, however, not made for samples B and C, but due to the fact that sample D was etched as well as samples B and C, sample D gives an indication of the probable values of the specific surface area of samples B and C according to the BET method.

The Hg method also gives a calculated value of the specific surface area. These values are shown for all of the grain samples according to the invention in table 1 and 2. As seen in table 1 and 2 there exists a difference between the measured values of the specific surface area according to the BET method and the calculated values according to the Hg method. These differences may be caused by the fact that:
- the calculation according to the Hg method is based on cylindrical and in size evenly pores;
- the results shown in table 1 and 2 indicate that the pore form may be different in different samples;
- the basic data used for the correction are results from a separately performed Hg analysis for each sample holder, and the compression may vary somewhat between different tests;
- the Hg method registers the size of the pore opening;
- the outer area of the particles affects the value minimally as a calculation of the specific surface area for non porous, spherical titanium particles with a diameter of 1 mm gives a value of 0.001 m²/g.

Two different grain start materials were used, namely one crude titanium sponge, e.g. produced by the Hunter process or Kroll, and as well one commercially available porous grain. The crude titanium sponge is hereinafter referred to as start material 1 and the commercially available porous grain as start material 2.

To obtain a first porous implant grain according to the invention a porous peripheral, but not most outer, part of the piece of the start material 1, i.e. crude titanium sponge was chosen, removed and chemically composition analysed for potential impurities. That part was then crushed and finally a first porous implant according to the present invention was selected by sieving and analysis in a batch, wherein the analysis was performed by gas absorption with nitrogen. Scanning electron microscopy (SEM) was also performed, which gives other pieces of information of value for the analysis.

This first grain according to the present invention, obtained from start material 1, is referred to as sample A in table 1 below.

A grain produced as above, i.e. a grain like sample A, was then treated in different ways according to the invention. The following was performed:
Sample B: etching in 3% $H_2O_2$ for 10 minutes
Sample C: etching in 30% $H_2O_2$ for 10 minutes
Sample D: etching in 30% $H_2O_2$ for 1 hour
Sample E: etching in 0.2% HF for 5 minutes
Sample F: oxidation in air for 2 hours at 900° C.

The results are summarized in table 1 below, and graphs are shown in drawings 1 to 7.

TABLE 1

Mean pore volume, mean pore diameter and specific surface area for grains according to the invention.

| Sample | Mean pore volume, (cm³/g) | Mean pore diameter, (μm) | Specific surface area, (m²/g) | |
|---|---|---|---|---|
| | | | Calculated (Hg method) | Measured (BET method) |
| A | 0.32 | 15 | 0.06 | 0.17 |
| B | 0.32 | 19 | 0.06 | — |
| C | 0.32 | 19 | 0.06 | — |
| D | 0.33 | 15 | 0.07 | 0.33 |
| E | 0.36 | 15, 0.15[1] | 0.24 | 0.42 |
| F | 0.13 | 70, 0.5 | 0.52 | 0.41 |

Note
[1]Very small part of the total pore volume

The mean pore volume of e.g. sample A can be seen from FIG. A1 as the finish value of the cumulative pore volume, that is 0.32 cm³/g. The same is of course applicable for samples B to F.

The mean pore volume, taken from the x axis, for the different samples corresponds in principle to the top value of the differential pore volume of the graphs in FIG. 2 of samples A to F. The top value of the differential pore volume of the graph of FIG. A2, sample A, corresponds to about 150,000 Ångström, i.e. 15 μm, as is pointed out in table 1. The same is of course applicable for the graphs of samples B to F.

Moreover, the areas below the graphs in FIG. 2 of samples A to F give a measurement of the specific surface areas. These values could be compared to each other, with reference to table 1.

As can be seen from the results, the etching with $H_2O_2$ was not as effective as HF in relation to increasing the specific surface area of the grain. When HF was used for etching the specific surface area increased from 0.17 to 0.42 m²/g. All the same, when 30% $H_2O_2$ was used for 1 hour the specific surface area also increased in comparison to sample A (compare the measured BET values of sample A and D). Moreover, the etching with HF gave two different values of the mean pore diameter (see table 1), which should be interpreted as a result of the formation of a new substantial fraction of smaller pores (0.15 μm) of the grain in addition to the fraction of larger pores (15 μm).

By the oxidation in air for 2 hours at 900° C., the specific surface area increased significantly, and the mean pore volume decreased somewhat. This is due to that there now exists another distribution of smaller but more pores, which in comparison leads to an increased specific surface area. In this case, as well as with the etching with HF, there were two different mean pore diameter values achieved. Drawing 10, FIG. F3, of the incremental intrusion vs. mean pore diameter shows this fact very clearly, where there exists two different top values of the incremental pore volume, i.e. it is a bimodal distribution, one for about 700,000 Ångström (70 μm) and one for about 5,000 Ångström (0.5 μm).

Start material 2 consisted of a commercially available grain. This grain is hereinafter referred to as sample G and this grain is of course not part of the scope of the present invention. This is also possible to see from the different values of this grain, when measured according to the Hg method and BET method. The commercially available grain, sample G, had a mean pore volume of 0.06 cm³/g, a mean pore diameter of 10 μm and a specific surface area according to the Hg method of 0.02 m²/g and 0.12 m²/g according to the BET method. The value of the specific surface area of the commercially available grain is in other words well outside the scope of the present invention in relation to the values of the specific surface area according to the BET method. The same goes if a comparison is made in relation to the Hg method.

The sample G, the commercially available grain, was then treated according to the invention to enhance the specific surface area, and accordingly enhance the anti-inflammatory and/or antibacterial effects. The following was performed from a commercially available grain, like sample G:

Sample H: etching in 0.2% HF for 5 minutes
Sample I: oxidation in air for 2 hours at 900° C.
The results are given in table 2 below.

TABLE 2

Mean pore volume, mean pore diameter and specific surface area for grains according to the invention.

| Sample | Mean pore volume, (cm³/g) | Mean pore diameter, (μm) | Specific surface area, (m²/g) | |
|---|---|---|---|---|
| | | | Calculated (Hg method) | Measured (BET method) |
| H | 0.07 | 75, 0.3[1] | 0.05 | 0.27 |
| I | 0.05 | 10-70, 0.3, 0.04-0.1 | 0.44 | 0.39 |

Note
[1]Very small part of the total pore volume

The mean pore volume of samples H and I, which are grains according to the invention and sample G, which is the start material 2, can be seen in the drawings 8-10 in the same way as for the other samples. The same goes for the mean pore volume, taken from the x axis, for the samples G to I.

Moreover, the areas below the graphs in FIG. 2 of samples G to I give a measurement of the specific surface areas. These values could be compared to each other, with reference to table 2.

As can be seen from the results, the etching with HF and the oxidation in air for 2 hours at 900° C. increased the specific surface area from 0.02 m²/g in sample G to 0.05 m²/g in grain sample H and 0.44 m²/g in grain sample 1, respectively. The values of the specific surface area of samples H and I are well inside the scope of the invention according to the BET method. This is of course not the fact for the commercially available grain, sample G (start material 2).

The grain sample H, treated with HF, has two different mean pore diameter values and the oxidised grain sample I is bimodal, just as the case for the comparable grain samples E and F.

The start material 2 (grain sample G) is a totally different grain in comparison to the untreated grain according to the invention (grain sample A). This can e.g. be seen by comparison of the mean pore volume values of grain sample G and A, where that value of sample G is 0.06 cm³/g and of sample A it is 0.32 cm³/g. The lower value of sample G is also the reason why the value of treated grain samples H and I according to the invention have lower mean pore volumes than grain samples A to F according to the invention. The real important value of the present invention, that is the specific surface area, is however high in all of the grain samples A to F and H and I according to the invention in comparison to grain sample G.

Example 2

Comparison Trial for Determination of the Anti-Inflammatory and/or Antibacterial Effects of Untreated Rains According to the Invention In a pilot experiment in rabbits the local bactericidal effects of untreated porous titanium granules according to the invention were compared to a commercially available bone substitute based on demineralized bone matrix. Under anesthesia the legs were shaved and a small incision made over the tibia bilaterally. A small pocket was bluntly dissected between the tibia and the tibialis anterior muscle. The two test materials were soaked with a diluted suspension of *Staphylococcus aureus* and 0.2 ml of each was placed into each rabbit. After 2 weeks the animals were euthanized and the local infection evaluated clinically. In 2 of 7 instances there was a clinical infection were the porous titanium granules according to the present invention were placed, whereas 6 of 7 sites with demineralized bone matrix were infected indicating a clear difference in bactericidal potential, that is anti-inflammatory and anti-bacterial effect, between the two materials (p=0.05, Fisher's exact test).

Example 3

Comparison Trial for Determination of the Anti-Inflammatory and/or Antibacterial Effects of $H_2O_2$ Treated Grains According to the Invention In a pilot experiment in 5 rabbits the local bactericidal effects of treated porous titanium granules according to the invention were compared to the effect of untreated porous titanium granules according to the invention. Under anesthesia the legs of the rabbits were shaved and a small incision made over the tibia bilaterally. A small pocket was bluntly dissected between the tibia and the tibialis anterior muscle. The two test materials were soaked with a diluted suspension of *Staphylococcus aureus* and 0.2 ml of each was placed into each rabbit. The untreated granule according to the invention was placed into the right legs of the rabbits and the $H_2O_2$ in the left ones. After 8 days the animals were euthanized and the local infection evaluated clinically. The clinical results are shown in table 3 below.

TABLE 3

Clinical results of comparison trial in relation to the effects of untreated vs. $H_2O_2$ treated granules according to the invention.

| Rabbit No. | Untreated granules, right legs | $H_2O_2$ treated granules, left legs |
|---|---|---|
| 1 | 0[2] | 0 |
| 2 | infection | 0 |

TABLE 3-continued

Clinical results of comparison trial in relation to the effects of untreated vs. $H_2O_2$ treated granules according to the invention.

| Rabbit No. | Untreated granules, right legs | $H_2O_2$ treated granules, left legs |
|---|---|---|
| 3 | infection | 0 |
| 4 | infection | 0 |
| 5 | infection | small infection |

Note
[2] A value of 0 indicates no infection

As is notable from the results, the anti-inflammatory and antibacterial effects of the $H_2O_2$ treated granules according to the present invention were enhanced in comparison to the untreated granules according to the invention.

The antibacterial effect of titanium depends on the presence of oxygen radicals. In the body such radicals are generated by white blood cells, especially by so called polymorphonuclear neutrophils. These produce a series of different radicals as a response to bacteria and this is a principle mechanism for bacterial killing by the host. The inventors have as mentioned investigated the antibacterial effect of various titanium granules by introducing the granules into rabbit tissue together with a small and controlled amount of *Staphylococcus Aureues*. After one week, the granules with surrounding tissue was harvested and disintegrated and plated on agar plates. The samples were evaluated for colony forming units (CFU), which is a measure of the number of bacteria in the sample. The inventors found a consistent decrease of the CFU from $10^6$-$10^7$ to a maximum of 100 for porous titanium granules treated with hydrogen peroxide, that is according to the present invention, compared to non-treated granules. Thus, the experiment confirms that the larger surface area is associated with increased radical functional interactions.

Example 4

Evaluation of Radical Capture in Experimental Systems Using Luminescence

Luminescence is light not generated by high temperatures alone. It is different from incandescence, in that it usually occurs at low temperatures and is thus a form of cold body radiation. It can be caused by, for example, chemical reactions, electrical energy, subatomic motions, or stress on a crystal. It represents a very sensitive way to detect presence of reactive oxygen radicals. Specifically luminal emits light when in reacting with hydrogen peroxide in the presence of an enzyme like peroxidase. Set up in the right way, the emitted light is proportional to the hydrogen peroxide concentration. By preincubating a hydrogen peroxide solution with samples of various modified biomaterials surfaces, the radical scavenging properties can be measured. Thus the emitted light was reduced to about 20% by preincubation with a grit blasted surface and 5% with a peroxide pretreated surface, that is in accordance with the present invention, compared to a machined titanium surface with the same diameter.

Radical capture is also something that may aid the ingrowth and growth of bone tissue (bone cells) and connective tissue into the pores of the implant according to the present invention.

CONCLUSIONS

To the inventors' great surprise, they found out that, not only the risk of developing inflammations/infections are diminished substantially, when using titanium, one or more titanium oxides or titanium alloy grains or granules according to the invention as implants, but also that these implants themselves have the ability to eliminate already inflamed/infected sites, when implanted in such sites (see examples 2 and 3). In other words, implants of titanium, one or more titanium oxides or titanium alloy according to the invention are applicable to inflamed sites, e.g. in the neighborhood of other titanium implants to cure inflammations and infections and ward off bacterial attacks. The implant according to the invention may e.g. be used for control of rheumatic joint inflammation, periodontitis, or for orthopaedic treatment, e.g. of bone infections (osteomyelites).

The implant according to the invention can also be successfully used in alveolar fillings and apical granulomas with eradication of infection and with remarkably little inflammatory reaction. Moreover, the implant according to the invention is applicable for treatment of local inflammations and infections in general in a human or animal body, however, especially of bone infections. The implants according to the invention are applicable to be introduced in sites of a human or animal body where there is a potential risk for infection or inflammation. One example is sites of the bodies where other medical devices, e.g. catheters and other skin or mucosa penetrating implants, are introduced. Specific examples of possible conditions to be treated are, as mentioned, periodontitis, periimplantitis and osteitis.

As notable from the results, an implant according to the present invention, that is comprising at least one grain or granule, is effective in relation to anti-inflammatory and antibacterial effect. This is valid for the untreated grain or granule of the present invention (see example 2), when compared to another implant material, but the effect is enhanced when the grains or granules are treated according to the invention (see example 3).

REFERENCES

1. Sittig C, Textor M, Spencer N D, Wieland M, Vallotton P H. Surface characterization of implant materials c.p. Ti, Ti-6Al-7Nb and Ti-6Al-4V with different pretreatments. J Mater Sci Mater Med 1999; 10(1):35-46.
2. Suzuki R, Muyco J, McKittrick J, Frangos J A. Reactive oxygen species inhibited by titanium oxide coatings. J Biomed Mater Res A 2003; 66(2):396-402.
3. Scharnweber D, Beutner R, Rossler S, Worch H. Electrochemical behavior of titanium-based materials—are there relations to biocompatibility? J Mater Sci Mater Med 2002; 13(12):1215-20.
4. Zhang F, Zheng Z, Chen Y, Liu X, Chen A, Jiang Z. In vivo investigation of blood compatibility of titanium oxide films. J Biomed Mater Res 1998; 42(1):128-33.
5. Tengvall P, Lundstrom I, Sjoqvist L, Elwing H, Bjursten L M. Titanium-hydrogen peroxide interaction: model studies of the influence of the inflammatory response on titanium implants. Biomaterials 1989; 10(3):166-75.
6. Tengvall P, Elwing H, Sjoqvist L, Lundstrom I, Bjursten L M. Interaction between hydrogen peroxide and titanium: a possible role in the biocompatibility of titanium. Biomaterials 1989; 10(2): 118-20.
7. Ragai J. Trapped radicals in titania gels. Nature 1987; 325(6106):703-5.
8. Wick P K, Kissner R, Koppenol W H. Kinetics evidence for a complex between peroxynitrous acid and titanium(IV). Inorg Chem 2004; 43(16):4805-7.
9. Tengvall P, Lundstrom I. Physico-chemical considerations of titanium as a biomaterial. Clin Mater 1992; 9(2):115-34.

10. Sundgren J-E, Bodo P, Lundstrom I. Auger electron spectroscopic studies of the interface between human tissue and implants of titanium and stainless steel. J Colloid Interface Sci 1986; 110(1):9-20.
11. Guang Pu Xue Yu Guang Pu Fen Xi. 2002 October; 22(5):783-6. Study on nanophase anatase-rutile transition with Raman spectrum.

The invention claimed is:

1. An implant with anti-inflammatory or antibacterial effects, or both, for implantation in a human or an animal body,
the implant comprising a set of porous grains or granules, wherein at least a plurality of the porous grains or granules:
comprise titanium, one or more titanium oxides or titanium alloy and have a titanium oxide layer on their surface;
have a mean length from one side to the opposite side, through a geometrical centre, of at least 200 µm and up to 5 mm;
have a mean specific surface area of at least 0.15 m$^2$/g according to the BET method.

2. The implant according to claim 1, wherein the plurality of the porous grains or granules have a mean length from one side to the opposite side, through a geometrical centre, of at least 200 µm and up to 2 mm.

3. The implant according to claim 1, wherein the plurality of the porous grains or granules have been treated with at least one fluoric compound, fluoride acids, hydrochloric acid, sulphuric acid, phosphorous acid, a peroxide compound chosen from hydrogen peroxide ($H_2O_2$) and organic peroxides, or oxalic acids, or a combination thereof, or has been dry etched with fluorinated or chlorinated gases.

4. The implant according to claim 3, wherein the fluoric compound is any type of fluoric acid, hydrofluoric acid in combination with nitric acid, ammonium fluoride, ammonium bifluoride, also in combination with nitric acid, or hydrogen fluoride (HF).

5. The implant according to claim 3, wherein the concentration is from 0.05 to 1.0% for fluoride acids, from 0.5 to 30.0% for hydrogen peroxides and from 0.2 to 20.0% for oxalic acids.

6. The implant according to claim 5, wherein the concentration is about 0.2% for fluoride acids, about 30% for hydrogen peroxides and about 10% for oxalic acids.

7. The implant according to any one of claims 1-6, wherein the plurality of the porous grains or granules have been oxidised by heat treatment in oxidising atmosphere at temperatures between 20 and 1000° C. and/or by electrochemical procedure.

8. The implant according to any one of claims 1-6, wherein the plurality of the porous grains or granules have been anodically oxidized using spark erosion to increase the surface area.

9. The implant according to any one of claims 1-6, wherein the plurality of the porous grains or granules have been produced according to a spark erosion procedure where the plurality of the porous grains or granules have been brought into contact with an anode using a flexible net or porous sponge-like structure.

10. The implant according to any one of claims 1-6, wherein the plurality of the porous grains or granules include nanotubes of titanium oxide, formed by a pre-treatment involving anodic oxidation, on their surface.

11. The implant according to any one of claims 1-6, wherein the plurality of the porous grains or granules include nanotubes of titanium oxide, formed by a pre-treatment involving anodic oxidation, on their surface, in an electrolyte solution comprising hydrofluoric acid (HF), potassium fluoride (KF), sodium fluoride (NaF), glycerol, $(NH_4)_2SO_4$ or $(NH_4)F$ or a combination thereof.

12. The implant according to any one of claims 1-6, wherein the plurality of the porous grains or granules have been heat treated in inert atmosphere or vacuum at a temperature of 500° C. or above, but below the melting point of the titanium, one or more titanium oxides or the titanium alloy.

13. The implant according to any one of claims 1-6, wherein the plurality of the porous grains or granules have been treated with HF or $H_2O_2$ and has a mean specific surface area of at least 0.25 m$^2$/g according to the BET method.

14. The implant according to any one of claims 1-6, wherein the plurality of the porous grains or granules have been treated with HF and has a mean specific surface area of at least 0.40 m$^2$/g according to the BET method.

15. The implant according to claim 1, wherein the plurality of the porous grains or granules have been oxidised, has a titanium oxide layer on their surface with a substantial thickness of at least 500 nm and is yellowish and/or whitish.

16. The implant according to claim 15, wherein the plurality of the porous grains or granules include an, at least partial, outer layer of titanium or titanium alloy having a thickness in the range of 30-500 nm.

17. The implant according to any one of claims 1-6, wherein the plurality of the porous grains or granules have been oxidised and has a mean specific surface area of at least 0.40 m$^2$/g according to the BET method.

18. The implant according to claim 1, wherein at least one substance, which substance is biologically active, is filled into the pores of the plurality of the porous grains or granules and/or is bound to the surface of the plurality of the porous grains or granules.

19. The implant according to claim 18, wherein the at least one substance comprises antibiotics, factors promoting tissue growth or regeneration, or a combination thereof.

20. The implant according to claim 19, wherein the at least one substance is bone morphogenic factor, andronate, alfa-keto glutarate, simvastatin, gentamicin or synthetic type I collagen, or a combination thereof.

21. The implant according to claim 19, wherein the at least one substance is at least one active enamel substance, which active enamel substance is enamel matrix, enamel matrix derivatives or enamel matrix proteins or combinations thereof.

22. The implant according to claim 19, wherein the at least one substance is at least one active enamel substance selected from enameling, amelogenins, non-amelogenins, proline-rich nonamelogenins, amelins, tuftelins, tuft proteins, salivary proteins, dentinsialoprotein DSP, dentinsialophosphoprotein DSPP, and derivatives thereof and combinations and mixtures thereof.

23. The implant according to claim 21 or 22, wherein the at least one active enamel substance is mixed with propylene glycole alginate (PGA).

24. The implant according to claim 1, wherein the implant is additionally admixed with at least one fluid vehicle.

25. The implant according to claim 24, wherein the at least one fluid vehicle is chosen from NaCl (aq), hyaluronic acid, PEG, propylene glycole alginate (PGA), titanium peroxy gel, methyl cellulose, carbomethyl cellulose, dextran, a high viscous polymeric gel, and a protein solution, or a combination thereof.

26. The implant according to claim 24 or 25, wherein the at least one fluid vehicle is comprised in a gel having a melting temperature above ambient temperature and below 37° C.

(body temperature), which gel optionally comprises at least one of NaCl (aq), hyaluronic acid, PEG, propylene glycole alginate (PGA), titanium peroxy gel, methyl cellulose, carbomethyl cellulose, dextran, a high viscous polymeric gel, and a protein solution.

27. A method for treating a condition comprising an inflammation or/and an infection present in a human or animal body, wherein an implant according to any one of claim 1-6, 15, 16, 18-22, 24 or 25 is brought into contact with an inflamed/infected site in the human or animal body.

28. A method for treating a condition comprising an inflammation or/and an infection present in a human or animal body, wherein an implant according to any one of claim 1-6, 15, 16, 18-22, 24 or 25, of which implant the plurality of the porous grains or granules include nanotubes of titanium oxide, formed by a pre-treatment involving anodic oxidation, on their surface, is brought into contact with an inflamed/infected site in the human or animal body.

29. The method according to claim 27, wherein the condition is chosen from periodontitis, periimplantitis and osteitis, and wherein the implant is brought into contact with a site which is typical for the condition being treated.

30. The method according to claim 27, wherein the implant is treated in vivo by UV radiation with a wavelength $\lambda$ of 200-500 nm.

31. The method according to claim 27, wherein the implant is treated in vivo by UV radiation with a wavelength $\lambda$ of 250-350 nm.

32. A method for producing implants according to claim 1 from a piece of a crude titanium or titanium alloy sponge, comprising the steps of:

choosing and removing a porous peripheral, but not most outer, part of the piece of the crude titanium or titanium alloy sponge;
analysing that part in view of the chemical composition for potential impurities;
crushing that part, if pure, and;
selecting the implants by sieving and analysis in batches, the analysis in batches being performed by scanning electron microscopy (SEM) or by gas absorption with nitrogen, the Hg method and/or the BET method.

33. The implant according to claim 1, wherein the plurality of the porous grains or granules have a mean specific surface area of 0.15 $m^2/g$ to 0.44 $m^2/g$ according to the BET method.

34. A population of grains or granules having anti-inflammatory or antibacterial effects, or both, for implantation in a human or an animal body, the population of grains or granules comprising:
a plurality of porous grains or granules which
comprise titanium, one or more titanium oxides or titanium alloy and have a titanium oxide layer on their surface;
have a mean length from one side to the opposite side, through a geometrical centre, of at least 200 μm and up to 5 mm; and
have a mean specific surface area of at least 0.15 $m^2/g$ according to the BET method.

35. The implant according to claim 34, wherein the plurality of the porous grains or granules have a mean specific surface area of 0.15 $m^2/g$ to 0.44 $m^2/g$ according to the BET method.

* * * * *